US008357111B2

(12) United States Patent
Caillouette et al.

(10) Patent No.: US 8,357,111 B2
(45) Date of Patent: Jan. 22, 2013

(54) METHOD AND SYSTEM FOR DESIGNING PATIENT-SPECIFIC ORTHOPAEDIC SURGICAL INSTRUMENTS

(75) Inventors: James Caillouette, Newport Beach, CA (US); Jose F. Guzman, Fort Wayne, IN (US); Jason T. Sherman, Warsaw, IN (US)

(73) Assignee: DePuy Products, Inc., Warsaw, IN (US)

( * ) Notice: Subject to any disclaimer, the term of this patent is extended or adjusted under 35 U.S.C. 154(b) by 1300 days.

(21) Appl. No.: 11/865,013

(22) Filed: Sep. 30, 2007

(65) Prior Publication Data
US 2009/0088674 A1    Apr. 2, 2009

(51) Int. Cl.
G02B 6/00 (2006.01)
A61B 5/103 (2006.01)
A61B 5/117 (2006.01)
A61B 3/16 (2006.01)
A61F 5/00 (2006.01)
A61L 15/00 (2006.01)

(52) U.S. Cl. .............. 602/26; 385/12; 385/13; 600/301; 600/400; 600/587; 600/595; 602/5; 602/6; 602/12; 602/23; 602/75

(58) Field of Classification Search ................ 602/5, 12, 602/16, 23, 26; 385/12, 13; 600/595, 301, 600/400, 587
See application file for complete search history.

(56) References Cited

U.S. PATENT DOCUMENTS

| | | |
|---|---|---|
| 2,702,550 A | 2/1955 | Rowe |
| 3,229,372 A | 1/1966 | Quashnock et al. |
| 3,298,410 A | 1/1967 | Noboru |
| 3,624,747 A | 11/1971 | McKnight et al. |
| 3,698,017 A | 10/1972 | Scales et al. |
| 3,774,244 A | 11/1973 | Walker |
| 3,816,855 A | 6/1974 | Saleh |
| 3,840,904 A | 10/1974 | Tronzo |
| 3,869,731 A | 3/1975 | Waugh et al. |
| 3,901,298 A | 8/1975 | Eby |
| 3,903,549 A | 9/1975 | Deyerle |

(Continued)

FOREIGN PATENT DOCUMENTS

CA    2447694    12/2002

(Continued)

OTHER PUBLICATIONS

Talbot et al., "A home-based pedometer-driven walking program to increase physical activity in older adults with osteoarthritis of the knee: a preliminary study," Journal of the American Geriatrics Society, Mar. 2003, vol. 51, No. 3.

(Continued)

Primary Examiner — Patricia Bianco
Assistant Examiner — Brandon L Jackson
(74) Attorney, Agent, or Firm — Barnes & Thornburg LLP

(57) ABSTRACT

A method and system for designing a patient-specific orthopaedic surgical instrument includes coupling a knee sleeve to a leg of the patient. The knee sleeve includes sensors configured to generate sensor data indicate of the position of the respective sensor. The method also include determining angulation data indicative of the angulation of the knee based on the sensor data. The angulation data may be indicative of, for example, the ligament laxity of the knee. The method may also include generating a medical image(s) of the knee. The design of the patient-specific orthopaedic surgical instrument is determined based on the angulation data and the medical image(s).

17 Claims, 11 Drawing Sheets

U.S. PATENT DOCUMENTS

| | | |
|---|---|---|
| 3,920,022 A | 11/1975 | Pastor |
| 3,941,127 A | 3/1976 | Froning |
| 3,965,950 A | 6/1976 | MacDonald |
| 3,994,287 A | 11/1976 | Turp et al. |
| 4,055,862 A | 11/1977 | Farling |
| 4,081,866 A | 4/1978 | Upshaw et al. |
| 4,085,466 A | 4/1978 | Goodfellow et al. |
| 4,140,161 A | 2/1979 | Russo et al. |
| 4,197,886 A | 4/1980 | MacDonald |
| 4,311,145 A | 1/1982 | Esty et al. |
| 4,349,018 A | 9/1982 | Chambers |
| 4,373,709 A | 2/1983 | Whitt |
| 4,386,609 A | 6/1983 | Mongeon |
| 4,400,833 A | 8/1983 | Kurland |
| 4,436,684 A | 3/1984 | White |
| D273,895 S | 5/1984 | Kenna |
| D274,091 S | 5/1984 | Kenna |
| 4,475,549 A | 10/1984 | Oh |
| 4,501,269 A | 2/1985 | Bagby |
| 4,506,393 A | 3/1985 | Murphy |
| 4,509,518 A | 4/1985 | McGarry et al. |
| 4,534,365 A | 8/1985 | Bonetta et al. |
| 4,545,375 A | 10/1985 | Cline |
| 4,549,555 A * | 10/1985 | Fraser et al. .................. 600/595 |
| 4,562,598 A | 1/1986 | Kranz |
| 4,565,192 A | 1/1986 | Shapiro |
| 4,567,886 A | 2/1986 | Petersen |
| 4,574,794 A | 3/1986 | Cooke et al. |
| 4,583,554 A * | 4/1986 | Mittelman et al. ............ 600/587 |
| 4,583,555 A * | 4/1986 | Malcom et al. ............... 600/595 |
| 4,621,630 A | 11/1986 | Kenna |
| 4,632,111 A | 12/1986 | Roche |
| 4,641,648 A | 2/1987 | Shapiro |
| 4,646,729 A | 3/1987 | Kenna et al. |
| 4,662,372 A | 5/1987 | Sharkany et al. |
| 4,663,720 A | 5/1987 | Duret et al. |
| 4,695,283 A | 9/1987 | Aldinger |
| 4,703,751 A | 11/1987 | Pohl |
| 4,704,686 A | 11/1987 | Aldinger |
| 4,711,233 A | 12/1987 | Brown |
| 4,718,413 A | 1/1988 | Johnson |
| 4,718,916 A | 1/1988 | Morscher |
| 4,719,907 A | 1/1988 | Banko et al. |
| 4,721,104 A | 1/1988 | Kaufman et al. |
| 4,739,751 A | 4/1988 | Sapega et al. |
| 4,759,350 A | 7/1988 | Dunn et al. |
| 4,787,383 A | 11/1988 | Kenna |
| 4,800,874 A | 1/1989 | David et al. |
| 4,822,365 A | 4/1989 | Walker et al. |
| 4,834,080 A | 5/1989 | Brown |
| 4,834,757 A | 5/1989 | Brantigan |
| 4,838,891 A | 6/1989 | Branemark et al. |
| 4,841,975 A | 6/1989 | Woolson |
| 4,846,161 A | 7/1989 | Roger |
| 4,860,735 A | 8/1989 | Davey et al. |
| 4,888,022 A | 12/1989 | Huebsch |
| 4,893,619 A | 1/1990 | Dale et al. |
| 4,896,663 A | 1/1990 | Vandewalls |
| 4,911,721 A | 3/1990 | Andergaten 3 et al. |
| 4,913,163 A * | 4/1990 | Roger et al. .................. 600/595 |
| 4,927,422 A | 5/1990 | Engelhardt |
| 4,935,023 A | 6/1990 | Whiteside et al. |
| 4,936,852 A | 6/1990 | Kent et al. |
| 4,936,862 A | 6/1990 | Walker et al. |
| 4,952,213 A | 8/1990 | Bowman et al. |
| 4,959,066 A | 9/1990 | Dunn et al. |
| 4,961,740 A | 10/1990 | Ray et al. |
| 4,961,954 A | 10/1990 | Goldberg et al. |
| 4,964,865 A | 10/1990 | Burkhead et al. |
| 4,976,737 A | 12/1990 | Leake |
| 4,979,949 A | 12/1990 | Matsen, III et al. |
| 4,979,957 A | 12/1990 | Hodorek |
| 4,985,037 A | 1/1991 | Petersen |
| 5,002,579 A | 3/1991 | Copf et al. |
| 5,007,912 A | 4/1991 | Albrektsson et al. |
| 5,007,936 A | 4/1991 | Woolson |
| 5,015,247 A | 5/1991 | Michelson |
| 5,030,221 A | 7/1991 | Buechel et al. |
| 5,032,132 A | 7/1991 | Matsen, III et al. |
| 5,035,700 A | 7/1991 | Kenna |
| 5,041,117 A | 8/1991 | Engelhardt |
| 5,053,037 A | 10/1991 | Lackey |
| 5,053,039 A | 10/1991 | Hofmann et al. |
| 5,060,678 A | 10/1991 | Bauman et al. |
| 5,061,286 A | 10/1991 | Lyle |
| 5,062,843 A | 11/1991 | Mahony, III |
| 5,067,964 A | 11/1991 | Richmond et al. |
| 5,084,050 A | 1/1992 | Draenert |
| 5,086,401 A | 2/1992 | Glassman et al. |
| 5,092,869 A | 3/1992 | Waldron |
| 5,098,383 A | 3/1992 | Hemmy et al. |
| 5,098,436 A | 3/1992 | Ferrante et al. |
| 5,098,437 A | 3/1992 | Kashuba et al. |
| 5,100,689 A | 3/1992 | Goldberg et al. |
| 5,111,987 A | 5/1992 | Moeinzadeh et al. |
| 5,122,144 A | 6/1992 | Bert et al. |
| 5,123,906 A | 6/1992 | Kelman |
| 5,129,908 A | 7/1992 | Petersen |
| 5,129,909 A | 7/1992 | Sutherland |
| 5,133,660 A | 7/1992 | Fenick |
| 5,133,760 A | 7/1992 | Petersen et al. |
| 5,147,365 A | 9/1992 | Whitlock et al. |
| 5,150,304 A | 9/1992 | Berchem et al. |
| 5,152,744 A | 10/1992 | Krause et al. |
| 5,152,778 A | 10/1992 | Bales, Jr. et al. |
| 5,154,717 A | 10/1992 | Matsen, III et al. |
| 5,171,243 A | 12/1992 | Kashuba et al. |
| 5,171,244 A | 12/1992 | Caspari et al. |
| 5,171,276 A | 12/1992 | Caspari et al. |
| 5,174,300 A | 12/1992 | Bales et al. |
| 5,176,684 A | 1/1993 | Ferrante et al. |
| 5,176,702 A | 1/1993 | Bales et al. |
| 5,186,174 A | 2/1993 | Schloendorff et al. |
| 5,192,327 A | 3/1993 | Brantigan |
| 5,197,971 A | 3/1993 | Bonutti |
| 5,197,987 A | 3/1993 | Koch et al. |
| 5,207,680 A | 5/1993 | Dietz et al. |
| 5,207,692 A | 5/1993 | Kraus et al. |
| 5,217,463 A | 6/1993 | Mikhail |
| 5,228,459 A | 7/1993 | Caspari et al. |
| 5,234,433 A | 8/1993 | Bert et al. |
| 5,242,448 A | 9/1993 | Pettine et al. |
| 5,258,032 A | 11/1993 | Bertin |
| 5,261,915 A | 11/1993 | Durlacher et al. |
| 5,263,498 A | 11/1993 | Caspari et al. |
| 5,263,987 A | 11/1993 | Shah |
| 5,269,785 A | 12/1993 | Bonutti |
| 5,273,524 A | 12/1993 | Fox et al. |
| 5,274,565 A | 12/1993 | Reuben |
| 5,275,603 A | 1/1994 | Ferrante et al. |
| 5,282,803 A | 2/1994 | Lackey |
| 5,285,773 A | 2/1994 | Bonutti et al. |
| 5,299,288 A | 3/1994 | Glassman et al. |
| 5,300,077 A | 4/1994 | Howell |
| 5,304,181 A | 4/1994 | Caspari et al. |
| 5,308,349 A | 5/1994 | Mikhail |
| 5,314,478 A | 5/1994 | Oka et al. |
| 5,314,482 A | 5/1994 | Goodfellow et al. |
| 5,320,529 A | 6/1994 | Pompa |
| 5,320,625 A | 6/1994 | Bertin |
| 5,322,505 A | 6/1994 | Krause et al. |
| 5,342,366 A | 8/1994 | Whiteside et al. |
| 5,342,367 A | 8/1994 | Ferrante et al. |
| 5,342,368 A | 8/1994 | Petersen |
| 5,344,423 A | 9/1994 | Dietz et al. |
| 5,344,458 A | 9/1994 | Bonutti |
| 5,360,446 A | 11/1994 | Kennedy |
| 5,364,402 A | 11/1994 | Mumme et al. |
| 5,368,858 A | 11/1994 | Hunziker |
| 5,370,692 A | 12/1994 | Fink et al. |
| 5,370,699 A | 12/1994 | Hood et al. |
| 5,382,249 A | 1/1995 | Fletcher |
| 5,383,937 A | 1/1995 | Mikhail |
| 5,390,683 A | 2/1995 | Pisharodi |
| 5,395,376 A | 3/1995 | Caspari et al. |
| 5,405,395 A | 4/1995 | Coates |
| 5,408,409 A | 4/1995 | Glassman et al. |

| Patent | Date | Inventor |
|---|---|---|
| D358,647 S | 5/1995 | Cohen et al. |
| 5,415,662 A | 5/1995 | Ferrante et al. |
| 5,417,694 A | 5/1995 | Marik et al. |
| 5,423,827 A | 6/1995 | Mumme et al. |
| 5,423,828 A | 6/1995 | Benson |
| 5,440,496 A | 8/1995 | Andersson et al. |
| 5,443,475 A | 8/1995 | Auerbach et al. |
| 5,445,639 A | 8/1995 | Kuslich et al. |
| 5,445,642 A | 8/1995 | McNulty et al. |
| 5,448,489 A | 9/1995 | Reuben |
| 5,452,407 A | 9/1995 | Crook |
| 5,454,816 A | 10/1995 | Ashby |
| 5,456,268 A | 10/1995 | Bonutti |
| 5,458,645 A | 10/1995 | Bertin |
| 5,462,549 A | 10/1995 | Glock |
| 5,472,415 A | 12/1995 | King et al. |
| 5,474,559 A | 12/1995 | Bertin et al. |
| 5,486,178 A | 1/1996 | Hodge |
| 5,490,854 A | 2/1996 | Fisher et al. |
| 5,496,324 A | 3/1996 | Barnes |
| 5,497,933 A | 3/1996 | DeFonzo et al. |
| 5,507,833 A | 4/1996 | Bohn |
| 5,510,066 A | 4/1996 | Fink et al. |
| 5,514,139 A | 5/1996 | Goldstein et al. |
| 5,514,143 A | 5/1996 | Bonutti et al. |
| 5,514,519 A | 5/1996 | Neckers |
| 5,518,680 A | 5/1996 | Cima et al. |
| 5,520,692 A | 5/1996 | Ferrante |
| 5,520,694 A | 5/1996 | Dance et al. |
| 5,520,695 A | 5/1996 | Luckman |
| 5,522,897 A | 6/1996 | King et al. |
| 5,527,317 A | 6/1996 | Ashby et al. |
| 5,539,649 A | 7/1996 | Walsh et al. |
| 5,540,695 A | 7/1996 | Levy |
| 5,542,947 A | 8/1996 | Treacy |
| 5,549,683 A | 8/1996 | Bonutti |
| 5,554,190 A | 9/1996 | Draenert |
| 5,560,096 A | 10/1996 | Stephens |
| 5,562,674 A | 10/1996 | Stalcup et al. |
| 5,562,675 A | 10/1996 | McNulty et al. |
| 5,569,163 A | 10/1996 | Francis et al. |
| 5,569,261 A | 10/1996 | Marik et al. |
| 5,571,110 A | 11/1996 | Matsen, III et al. |
| 5,578,037 A | 11/1996 | Sanders et al. |
| 5,578,039 A | 11/1996 | Vendrely et al. |
| 5,586,558 A | 12/1996 | Riley |
| 5,593,448 A | 1/1997 | Dong |
| 5,595,703 A | 1/1997 | Swaelens et al. |
| 5,597,379 A | 1/1997 | Haines et al. |
| 5,601,563 A | 2/1997 | Burke et al. |
| 5,607,431 A | 3/1997 | Dudasik et al. |
| 5,609,603 A | 3/1997 | Linden |
| 5,620,448 A | 4/1997 | Puddu |
| 5,624,444 A | 4/1997 | Wixon et al. |
| 5,632,745 A | 5/1997 | Schwartz |
| 5,634,927 A | 6/1997 | Houston et al. |
| 5,643,272 A | 7/1997 | Haines et al. |
| 5,649,947 A | 7/1997 | Auerbach et al. |
| 5,653,714 A | 8/1997 | Dietz et al. |
| 5,658,294 A | 8/1997 | Sederholm |
| 5,662,656 A | 9/1997 | White |
| 5,667,511 A | 9/1997 | Vendrely et al. |
| 5,667,512 A | 9/1997 | Johnson |
| 5,677,107 A | 10/1997 | Neckers |
| 5,681,316 A | 10/1997 | DeOrio et al. |
| 5,681,354 A | 10/1997 | Eckhoff |
| 5,682,886 A | 11/1997 | Delp et al. |
| 5,683,397 A | 11/1997 | Vendrely et al. |
| 5,683,398 A | 11/1997 | Carls et al. |
| 5,683,466 A | 11/1997 | Vitale |
| 5,688,279 A | 11/1997 | McNulty et al. |
| 5,688,280 A | 11/1997 | Booth, Jr. et al. |
| 5,690,635 A | 11/1997 | Matsen, III et al. |
| 5,701,370 A * | 12/1997 | Muhs et al. .................. 385/13 |
| 5,702,447 A | 12/1997 | Walch et al. |
| 5,702,460 A | 12/1997 | Carls et al. |
| 5,702,475 A | 12/1997 | Zahedi |
| 5,704,941 A | 1/1998 | Jacober et al. |
| 5,707,350 A | 1/1998 | Krause et al. |
| 5,716,360 A | 2/1998 | Baldwin et al. |
| 5,720,752 A | 2/1998 | Elliott et al. |
| 5,722,978 A | 3/1998 | Jenkins, Jr. |
| 5,725,376 A | 3/1998 | Poirier |
| 5,725,593 A | 3/1998 | Caracciolo |
| 5,733,292 A | 3/1998 | Gustilo et al. |
| 5,735,277 A | 4/1998 | Schuster |
| 5,748,767 A | 5/1998 | Raab |
| 5,749,875 A | 5/1998 | Puddu |
| 5,749,876 A | 5/1998 | Duvillier et al. |
| 5,755,803 A | 5/1998 | Haines et al. |
| 5,762,125 A | 6/1998 | Mastrorio |
| 5,768,134 A | 6/1998 | Swaelens et al. |
| 5,769,855 A | 6/1998 | Bertin et al. |
| 5,776,201 A | 7/1998 | Colleran et al. |
| 5,788,700 A | 8/1998 | Morawa et al. |
| 5,791,212 A | 8/1998 | Han |
| 5,792,143 A | 8/1998 | Samuelson et al. |
| 5,798,924 A | 8/1998 | Eufinger et al. |
| 5,799,055 A | 8/1998 | Peshkin et al. |
| 5,810,827 A | 9/1998 | Haines et al. |
| 5,810,831 A | 9/1998 | D'Antonio |
| 5,817,097 A | 10/1998 | Howard et al. |
| 5,824,085 A | 10/1998 | Sahay et al. |
| 5,860,980 A | 1/1999 | Axelson, Jr. et al. |
| 5,860,981 A | 1/1999 | Bertin et al. |
| 5,869,170 A | 2/1999 | Cima et al. |
| 5,871,018 A | 2/1999 | Delp et al. |
| 5,871,493 A | 2/1999 | Sjostrom et al. |
| 5,876,456 A | 3/1999 | Sederholm et al. |
| 5,879,354 A | 3/1999 | Haines et al. |
| 5,879,393 A | 3/1999 | Whiteside et al. |
| 5,879,402 A | 3/1999 | Lawes et al. |
| 5,885,296 A | 3/1999 | Masini |
| 5,885,297 A | 3/1999 | Matsen, III |
| 5,885,298 A | 3/1999 | Herrington et al. |
| 5,895,389 A | 4/1999 | Schenk et al. |
| 5,897,559 A | 4/1999 | Masini |
| 5,899,907 A | 5/1999 | Johnson |
| 5,899,914 A | 5/1999 | Zirps et al. |
| 5,901,060 A | 5/1999 | Schall et al. |
| 5,908,424 A | 6/1999 | Bertin et al. |
| 5,911,723 A | 6/1999 | Ashby et al. |
| 5,911,724 A | 6/1999 | Wehrli |
| 5,913,874 A | 6/1999 | Berns et al. |
| 5,916,219 A | 6/1999 | Matsuno et al. |
| 5,925,049 A | 7/1999 | Gustilo et al. |
| 5,942,370 A | 8/1999 | Neckers |
| 5,967,777 A | 10/1999 | Klein et al. |
| 5,976,149 A | 11/1999 | Masini |
| 5,980,526 A | 11/1999 | Johnson et al. |
| 5,989,261 A | 11/1999 | Walker et al. |
| 6,007,537 A | 12/1999 | Burkinshaw et al. |
| 6,012,456 A | 1/2000 | Schuerch |
| 6,019,767 A | 2/2000 | Howell |
| 6,022,350 A | 2/2000 | Ganem |
| 6,024,746 A | 2/2000 | Katz |
| 6,033,415 A | 3/2000 | Mittelstadt et al. |
| 6,056,754 A | 5/2000 | Haines et al. |
| 6,056,756 A | 5/2000 | Eng et al. |
| 6,059,831 A | 5/2000 | Braslow et al. |
| 6,063,095 A | 5/2000 | Wang et al. |
| 6,066,075 A | 5/2000 | Poulton |
| 6,077,270 A | 6/2000 | Katz |
| 6,077,287 A | 6/2000 | Taylor et al. |
| 6,080,196 A | 6/2000 | Bertin |
| 6,081,577 A | 6/2000 | Webber |
| 6,086,593 A | 7/2000 | Bonutti |
| 6,090,122 A | 7/2000 | Sjostrom et al. |
| 6,096,043 A | 8/2000 | Techiera et al. |
| 6,099,313 A | 8/2000 | Dorken et al. |
| 6,102,850 A | 8/2000 | Wang et al. |
| 6,106,529 A | 8/2000 | Techiera |
| 6,118,845 A | 9/2000 | Simon et al. |
| 6,120,509 A | 9/2000 | Wheeler |
| 6,120,510 A | 9/2000 | Albrektsson et al. |
| 6,120,544 A | 9/2000 | Grundei et al. |
| 6,126,690 A | 10/2000 | Ateshian et al. |
| 6,139,574 A | 10/2000 | Vacanti et al. |

| Patent No. | Date | Inventor |
|---|---|---|
| 6,156,069 A | 12/2000 | Amstutz |
| 6,156,070 A | 12/2000 | Incavo et al. |
| 6,159,246 A | 12/2000 | Mendes et al. |
| 6,161,080 A | 12/2000 | Aouni-Ateshian et al. |
| 6,176,874 B1 | 1/2001 | Vacanti et al. |
| 6,177,034 B1 | 1/2001 | Ferrone |
| 6,185,315 B1 | 2/2001 | Schmucker et al. |
| 6,187,010 B1 | 2/2001 | Masini |
| 6,195,615 B1 | 2/2001 | Lysen |
| 6,197,064 B1 | 3/2001 | Haines et al. |
| 6,198,794 B1 | 3/2001 | Peshkin et al. |
| 6,205,411 B1 | 3/2001 | DiGioia, III et al. |
| 6,206,927 B1 | 3/2001 | Fell et al. |
| 6,214,051 B1 | 4/2001 | Badorf et al. |
| 6,220,122 B1 | 4/2001 | Forsell et al. |
| 6,228,121 B1 | 5/2001 | Khalili |
| 6,241,735 B1 | 6/2001 | Marmulla |
| 6,244,141 B1 | 6/2001 | Han |
| 6,251,143 B1 | 6/2001 | Schwartz et al. |
| 6,254,604 B1 | 7/2001 | Howell |
| 6,258,127 B1 | 7/2001 | Schmotzer |
| 6,264,698 B1 | 7/2001 | Lawes et al. |
| 6,273,891 B1 | 8/2001 | Masini |
| 6,277,136 B1 | 8/2001 | Bonutti |
| 6,290,703 B1 | 9/2001 | Ganem |
| 6,290,704 B1 | 9/2001 | Burkinshaw et al. |
| 6,319,006 B1 | 11/2001 | Scherer et al. |
| 6,322,728 B1 | 11/2001 | Brodkin et al. |
| 6,325,806 B1 | 12/2001 | Fox |
| 6,327,491 B1 | 12/2001 | Franklin et al. |
| 6,343,987 B2 | 2/2002 | Hayama et al. |
| 6,354,011 B1 | 3/2002 | Albrecht |
| 6,361,506 B1 | 3/2002 | Saenger et al. |
| 6,382,975 B1 | 5/2002 | Poirier |
| 6,383,228 B1 | 5/2002 | Schmotzer |
| 6,391,251 B1 | 5/2002 | Keicher et al. |
| 6,395,005 B1 | 5/2002 | Lovell |
| 6,406,495 B1 | 6/2002 | Schoch |
| 6,409,722 B1 | 6/2002 | Hoey et al. |
| 6,427,698 B1 | 8/2002 | Yoon |
| D462,767 S | 9/2002 | Meyer et al. |
| 6,454,811 B1 | 9/2002 | Sherwood et al. |
| 6,458,135 B1 | 10/2002 | Harwin et al. |
| 6,459,948 B1 | 10/2002 | Ateshian et al. |
| 6,463,351 B1 | 10/2002 | Clynch |
| 6,468,280 B1 | 10/2002 | Saenger et al. |
| 6,468,289 B1 | 10/2002 | Bonutti |
| 6,478,799 B1 | 11/2002 | Williamson |
| 6,482,209 B1 | 11/2002 | Engh et al. |
| 6,503,255 B1 | 1/2003 | Albrektsson et al. |
| 6,510,334 B1 | 1/2003 | Schuster et al. |
| 6,514,259 B2 | 2/2003 | Picard et al. |
| 6,520,964 B2 | 2/2003 | Tallarida et al. |
| 6,530,958 B1 | 3/2003 | Cima et al. |
| 6,533,737 B1 | 3/2003 | Brosseau et al. |
| 6,554,837 B1 | 4/2003 | Hauri et al. |
| 6,554,838 B2 | 4/2003 | McGovern et al. |
| 6,556,008 B2 | 4/2003 | Thesen |
| 6,558,391 B2 | 5/2003 | Axelson et al. |
| 6,567,681 B1 | 5/2003 | Lindequist |
| 6,575,980 B1 | 6/2003 | Robie et al. |
| 6,575,982 B1 | 6/2003 | Bonutti |
| 6,591,581 B2 | 7/2003 | Schmieding |
| 6,602,259 B1 | 8/2003 | Masini |
| 6,626,945 B2 | 9/2003 | Simon et al. |
| 6,629,999 B1 | 10/2003 | Serafin, Jr. |
| 6,632,225 B2 | 10/2003 | Sanford et al. |
| 6,635,073 B2 | 10/2003 | Bonutti |
| 6,668,941 B2 | 12/2003 | Phillips et al. |
| 6,673,077 B1 | 1/2004 | Katz |
| 6,676,662 B1 | 1/2004 | Bagga et al. |
| 6,679,917 B2 | 1/2004 | Ek |
| 6,695,848 B2 | 2/2004 | Haines |
| 6,697,664 B2 | 2/2004 | Kienzle, III et al. |
| 6,701,174 B1 | 3/2004 | Krause et al. |
| 6,702,821 B2 | 3/2004 | Bonutti |
| 6,709,462 B2 | 3/2004 | Hanssen |
| 6,711,431 B2 | 3/2004 | Sarin et al. |
| 6,711,432 B1 | 3/2004 | Krause et al. |
| 6,712,824 B2 | 3/2004 | Millard et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,766,878 B2 | 7/2004 | Widmer et al. |
| 6,770,078 B2 | 8/2004 | Bonutti |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,814,735 B1 | 11/2004 | Zirngibl et al. |
| 6,827,723 B2 | 12/2004 | Carson |
| 6,905,514 B2 | 6/2005 | Carignan et al. |
| 6,916,324 B2 | 7/2005 | Sanford et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,979,299 B2 | 12/2005 | Peabody et al. |
| 6,990,220 B2 | 1/2006 | Ellis et al. |
| 6,994,549 B2 | 2/2006 | Brodkin et al. |
| 7,029,477 B2 | 4/2006 | Grimm |
| 7,029,479 B2 | 4/2006 | Tallarida et al. |
| 7,048,741 B2 | 5/2006 | Swanson |
| 7,050,877 B2 | 5/2006 | Iseki et al. |
| 7,060,074 B2 | 6/2006 | Rosa et al. |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,141,053 B2 | 11/2006 | Rosa et al. |
| 7,166,063 B2 * | 1/2007 | Rahman et al. .................. 482/8 |
| 7,172,597 B2 | 2/2007 | Sanford |
| 7,172,599 B2 | 2/2007 | Steffensmeier et al. |
| 7,175,435 B2 | 2/2007 | Andersson et al. |
| 7,176,466 B2 | 2/2007 | Rousso et al. |
| 7,184,814 B2 | 2/2007 | Lang et al. |
| 7,194,295 B2 | 3/2007 | Vilsmeier |
| 7,198,628 B2 | 4/2007 | Ondrla et al. |
| 7,239,908 B1 | 7/2007 | Alexander et al. |
| 7,255,702 B2 | 8/2007 | Serra et al. |
| 7,258,701 B2 | 8/2007 | Aram et al. |
| 7,261,719 B1 | 8/2007 | Twomey et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,371,260 B2 | 5/2008 | Malinin |
| 7,383,164 B2 | 6/2008 | Aram et al. |
| 7,388,972 B2 | 6/2008 | Kitson |
| 7,392,076 B2 | 6/2008 | Moctezuma de La Barrera |
| 7,427,272 B2 | 9/2008 | Richard et al. |
| 7,474,223 B2 | 1/2009 | Nycz et al. |
| 7,481,780 B2 * | 1/2009 | De Guise et al. ............ 600/595 |
| 7,488,324 B1 | 2/2009 | Metzger et al. |
| 7,527,631 B2 | 5/2009 | Maroney et al. |
| 7,534,263 B2 | 5/2009 | Burdulis, Jr. et al. |
| 7,539,243 B1 | 5/2009 | Toifl et al. |
| 7,542,791 B2 | 6/2009 | Mire et al. |
| 7,575,602 B2 | 8/2009 | Amirouche et al. |
| 7,582,091 B2 | 9/2009 | Duncan et al. |
| 7,591,821 B2 | 9/2009 | Kelman |
| 7,601,155 B2 | 10/2009 | Peterson |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,634,119 B2 | 12/2009 | Tsougarakis et al. |
| 7,651,501 B2 | 1/2010 | Penenberg et al. |
| 7,661,170 B2 * | 2/2010 | Goode et al. .................. 12/1 R |

| | | |
|---|---|---|
| 7,695,477 B2 | 4/2010 | Creger et al. |
| 7,704,253 B2 | 4/2010 | Bastian et al. |
| 7,717,956 B2 | 5/2010 | Lang |
| 7,769,422 B2 * | 8/2010 | DiSilvestro et al. .......... 600/407 |
| 7,780,672 B2 | 8/2010 | Metzger |
| 7,796,791 B2 | 9/2010 | Tsougarakis et al. |
| 7,799,077 B2 | 9/2010 | Lang et al. |
| 7,806,896 B1 | 10/2010 | Bonutti |
| 7,824,181 B2 | 11/2010 | Sers |
| 7,935,119 B2 | 5/2011 | Ammann et al. |
| 7,963,968 B2 | 6/2011 | Dees, Jr. |
| 7,967,868 B2 | 6/2011 | White et al. |
| 7,981,158 B2 | 7/2011 | Fitz et al. |
| 2001/0005797 A1 | 6/2001 | Barlow et al. |
| 2001/0018589 A1 | 8/2001 | Muller |
| 2001/0020143 A1 | 9/2001 | Stark et al. |
| 2001/0034554 A1 | 10/2001 | Pappas |
| 2001/0037155 A1 | 11/2001 | Merchant |
| 2002/0007294 A1 | 1/2002 | Bradbury et al. |
| 2002/0024450 A1 | 2/2002 | Townsend et al. |
| 2002/0029038 A1 | 3/2002 | Haines |
| 2002/0029045 A1 | 3/2002 | Bonutti |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0143279 A1 * | 10/2002 | Porier et al. .................... 602/16 |
| 2002/0147415 A1 | 10/2002 | Martelli |
| 2002/0173797 A1 | 11/2002 | Van Zile et al. |
| 2002/0183760 A1 | 12/2002 | McGovern et al. |
| 2002/0198529 A1 | 12/2002 | Masini |
| 2002/0198531 A1 | 12/2002 | Millard et al. |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0028196 A1 | 2/2003 | Bonutti |
| 2003/0055501 A1 | 3/2003 | Fell et al. |
| 2003/0055502 A1 | 3/2003 | Lang et al. |
| 2003/0069897 A1 | 4/2003 | Roy et al. |
| 2003/0100906 A1 | 5/2003 | Rosa et al. |
| 2003/0100907 A1 | 5/2003 | Rosa et al. |
| 2003/0109784 A1 | 6/2003 | Loh et al. |
| 2003/0120183 A1 | 6/2003 | Simmons |
| 2003/0130665 A1 | 7/2003 | Pinczewski et al. |
| 2003/0158606 A1 | 8/2003 | Coon et al. |
| 2003/0171757 A1 | 9/2003 | Coon et al. |
| 2003/0212403 A1 | 11/2003 | Swanson |
| 2003/0216669 A1 | 11/2003 | Lang et al. |
| 2003/0216741 A1 | 11/2003 | Sanford et al. |
| 2003/0220641 A1 | 11/2003 | Thelen et al. |
| 2003/0225413 A1 | 12/2003 | Sanford et al. |
| 2004/0039259 A1 | 2/2004 | Krause et al. |
| 2004/0039395 A1 | 2/2004 | Coon et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102785 A1 | 5/2004 | Hodorek et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138670 A1 | 7/2004 | Metzger |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0185422 A1 | 9/2004 | Orth et al. |
| 2004/0204760 A1 | 10/2004 | Fitz et al. |
| 2004/0220583 A1 | 11/2004 | Pieczynski et al. |
| 2004/0236424 A1 | 11/2004 | Berez et al. |
| 2004/0243481 A1 | 12/2004 | Bradbury et al. |
| 2004/0249385 A1 | 12/2004 | Faoro |
| 2004/0249675 A1 | 12/2004 | Stark et al. |
| 2004/0254584 A1 | 12/2004 | Sarin et al. |
| 2004/0260301 A1 | 12/2004 | Lionberger et al. |
| 2005/0015003 A1 | 1/2005 | Lachner et al. |
| 2005/0015022 A1 | 1/2005 | Richard et al. |
| 2005/0027303 A1 | 2/2005 | Lionberger et al. |
| 2005/0027361 A1 | 2/2005 | Reiley |
| 2005/0037320 A1 | 2/2005 | Poirier |
| 2005/0043835 A1 | 2/2005 | Christensen |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0065628 A1 | 3/2005 | Roose |
| 2005/0070897 A1 | 3/2005 | Petersen |
| 2005/0075641 A1 | 4/2005 | Singhatat et al. |
| 2005/0096535 A1 | 5/2005 | de la Barrera |
| 2005/0113840 A1 | 5/2005 | Metzger et al. |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0133955 A1 | 6/2005 | Christensen |
| 2005/0137708 A1 | 6/2005 | Clark |
| 2005/0148843 A1 | 7/2005 | Roose |
| 2005/0149042 A1 | 7/2005 | Metzger |
| 2005/0170311 A1 | 8/2005 | Tardieu et al. |
| 2005/0171545 A1 | 8/2005 | Walsh et al. |
| 2005/0177170 A1 | 8/2005 | Fisher et al. |
| 2005/0203536 A1 | 9/2005 | Laffargue et al. |
| 2005/0203540 A1 | 9/2005 | Broyles |
| 2005/0222573 A1 | 10/2005 | Branch et al. |
| 2005/0234461 A1 | 10/2005 | Burdulis et al. |
| 2005/0234468 A1 | 10/2005 | Carson |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0261697 A1 | 11/2005 | Canonaco et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095049 A1 | 5/2006 | Zannis et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0142671 A1 | 6/2006 | Solak |
| 2006/0142774 A1 | 6/2006 | Metzger |
| 2006/0142778 A1 | 6/2006 | Dees |
| 2006/0155380 A1 | 7/2006 | Clemow et al. |
| 2006/0161167 A1 | 7/2006 | Myers et al. |
| 2006/0184177 A1 | 8/2006 | Echeverri |
| 2006/0190086 A1 | 8/2006 | Clemow et al. |
| 2006/0195198 A1 | 8/2006 | James |
| 2006/0204932 A1 | 9/2006 | Haymann et al. |
| 2006/0210644 A1 | 9/2006 | Levin |
| 2006/0235421 A1 | 10/2006 | Rosa et al. |
| 2006/0245627 A1 | 11/2006 | Nagamune |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2007/0006887 A1 | 1/2007 | Frank |
| 2007/0015995 A1 | 1/2007 | Lang et al. |

| | | |
|---|---|---|
| 2007/0016209 A1 | 1/2007 | Ammann et al. |
| 2007/0027680 A1 | 2/2007 | Ashley et al. |
| 2007/0059665 A1 | 3/2007 | Orentlicher et al. |
| 2007/0066917 A1 | 3/2007 | Hodorek et al. |
| 2007/0083209 A1 | 4/2007 | Schenberger et al. |
| 2007/0083214 A1 | 4/2007 | Duncan et al. |
| 2007/0083266 A1 | 4/2007 | Lang |
| 2007/0100258 A1 | 5/2007 | Shoham et al. |
| 2007/0100462 A1 | 5/2007 | Lang et al. |
| 2007/0118055 A1 | 5/2007 | McCombs |
| 2007/0118243 A1 | 5/2007 | Schroeder et al. |
| 2007/0156066 A1 | 7/2007 | McGinley et al. |
| 2007/0162039 A1 | 7/2007 | Wozencroft |
| 2007/0173946 A1 | 7/2007 | Bonutti |
| 2007/0185498 A2 | 8/2007 | Lavallee |
| 2007/0198022 A1 | 8/2007 | Lang et al. |
| 2007/0203430 A1 | 8/2007 | Lang et al. |
| 2007/0203605 A1 | 8/2007 | Melton et al. |
| 2007/0213738 A1 | 9/2007 | Martin et al. |
| 2007/0219639 A1 | 9/2007 | Otto et al. |
| 2007/0225719 A1 | 9/2007 | Stone et al. |
| 2007/0233121 A1 | 10/2007 | Carson et al. |
| 2007/0233136 A1 | 10/2007 | Wozencroft |
| 2007/0233140 A1 | 10/2007 | Metzger et al. |
| 2007/0233141 A1 | 10/2007 | Park et al. |
| 2007/0233269 A1 | 10/2007 | Steines et al. |
| 2007/0233272 A1 | 10/2007 | Boyce et al. |
| 2007/0238069 A1 | 10/2007 | Lovald et al. |
| 2007/0239282 A1 | 10/2007 | Caylor et al. |
| 2007/0239481 A1 | 10/2007 | DiSilvestro et al. |
| 2007/0250169 A1 | 10/2007 | Lang |
| 2007/0253617 A1 | 11/2007 | Arata et al. |
| 2007/0255288 A1 | 11/2007 | Mahfouz et al. |
| 2007/0255412 A1 | 11/2007 | Hajaj et al. |
| 2007/0276224 A1 | 11/2007 | Lang et al. |
| 2007/0276400 A1 | 11/2007 | Moore et al. |
| 2007/0276501 A1 | 11/2007 | Betz et al. |
| 2007/0282451 A1 | 12/2007 | Metzger et al. |
| 2007/0288030 A1 | 12/2007 | Metzger et al. |
| 2008/0009952 A1 | 1/2008 | Hodge |
| 2008/0015602 A1 | 1/2008 | Axelson |
| 2008/0015605 A1 | 1/2008 | Collazo |
| 2008/0015607 A1 | 1/2008 | D'Alessio et al. |
| 2008/0021299 A1 | 1/2008 | Meulink |
| 2008/0021567 A1 | 1/2008 | Meulink et al. |
| 2008/0027563 A1 | 1/2008 | Johnson et al. |
| 2008/0051910 A1 | 2/2008 | Kammerzell et al. |
| 2008/0058945 A1 | 3/2008 | Hajaj et al. |
| 2008/0058947 A1 | 3/2008 | Earl et al. |
| 2008/0114370 A1 | 5/2008 | Schoenefeld et al. |
| 2008/0140209 A1 | 6/2008 | Iannotti et al. |
| 2008/0146969 A1 | 6/2008 | Kurtz |
| 2008/0147072 A1 | 6/2008 | Park et al. |
| 2008/0161815 A1 | 7/2008 | Schoenefeld et al. |
| 2008/0172125 A1 | 7/2008 | Ek |
| 2008/0183177 A1 | 7/2008 | Fox et al. |
| 2008/0195099 A1 | 8/2008 | Minas |
| 2008/0195107 A1 | 8/2008 | Cuckler et al. |
| 2008/0195216 A1 | 8/2008 | Philipp |
| 2008/0208200 A1 | 8/2008 | Crofford |
| 2008/0215059 A1 | 9/2008 | Carignan et al. |
| 2008/0228189 A1 | 9/2008 | Fox et al. |
| 2008/0234664 A1 | 9/2008 | May et al. |
| 2008/0234683 A1 | 9/2008 | May |
| 2008/0234685 A1 | 9/2008 | Gjerde |
| 2008/0234833 A1 | 9/2008 | Bandoh et al. |
| 2008/0243127 A1 | 10/2008 | Lang et al. |
| 2008/0257363 A1 | 10/2008 | Schoenefeld et al. |
| 2008/0262624 A1 | 10/2008 | White et al. |
| 2008/0269906 A1 | 10/2008 | Iannotti et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0294266 A1 | 11/2008 | Steinberg |
| 2008/0300600 A1 | 12/2008 | Guelat et al. |
| 2008/0306558 A1 | 12/2008 | Hakki |
| 2008/0312659 A1 | 12/2008 | Metzger et al. |
| 2008/0319448 A1 | 12/2008 | Lavallee et al. |
| 2009/0012526 A1 | 1/2009 | Fletcher |
| 2009/0018546 A1 | 1/2009 | Daley |
| 2009/0024131 A1 | 1/2009 | Metzger et al. |
| 2009/0043556 A1 | 2/2009 | Axelson et al. |
| 2009/0076371 A1 | 3/2009 | Lang et al. |
| 2009/0076512 A1 | 3/2009 | Ammann et al. |
| 2009/0082770 A1 | 3/2009 | Worner et al. |
| 2009/0087276 A1 | 4/2009 | Rose |
| 2009/0088674 A1 | 4/2009 | Caillouette et al. |
| 2009/0088753 A1 | 4/2009 | Aram et al. |
| 2009/0088754 A1 | 4/2009 | Aker et al. |
| 2009/0088755 A1 | 4/2009 | Aker et al. |
| 2009/0088758 A1 | 4/2009 | Bennett |
| 2009/0088759 A1 | 4/2009 | Aram et al. |
| 2009/0088760 A1 | 4/2009 | Aram et al. |
| 2009/0088761 A1 | 4/2009 | Roose et al. |
| 2009/0088763 A1 | 4/2009 | Aram et al. |
| 2009/0089034 A1 | 4/2009 | Penney et al. |
| 2009/0089081 A1 | 4/2009 | Haddad |
| 2009/0093816 A1 | 4/2009 | Roose et al. |
| 2009/0099567 A1 | 4/2009 | Zajac |
| 2009/0105837 A1 | 4/2009 | Lafosse et al. |
| 2009/0118736 A1 | 5/2009 | Kreuzer |
| 2009/0131941 A1 | 5/2009 | Park et al. |
| 2009/0131942 A1 | 5/2009 | Aker et al. |
| 2009/0138020 A1 | 5/2009 | Park et al. |
| 2009/0149965 A1 | 6/2009 | Quaid |
| 2009/0149977 A1 | 6/2009 | Schendel |
| 2009/0151736 A1 | 6/2009 | Belcher et al. |
| 2009/0157083 A1 | 6/2009 | Park et al. |
| 2009/0163922 A1 | 6/2009 | Meridew et al. |
| 2009/0163923 A1 | 6/2009 | Flett et al. |
| 2009/0164024 A1 | 6/2009 | Rudan et al. |
| 2009/0187193 A1 | 7/2009 | Maroney et al. |
| 2009/0209884 A1 | 8/2009 | Van Vorhis et al. |
| 2009/0209961 A1 | 8/2009 | Ferrante et al. |
| 2009/0222014 A1 | 9/2009 | Bojarski et al. |
| 2009/0222015 A1 | 9/2009 | Park et al. |
| 2009/0222016 A1 | 9/2009 | Park et al. |
| 2009/0228016 A1 | 9/2009 | Alvarez et al. |
| 2009/0234360 A1 | 9/2009 | Alexander |
| 2009/0248044 A1 | 10/2009 | Amiot et al. |
| 2009/0254093 A1 | 10/2009 | White et al. |
| 2009/0254367 A1 | 10/2009 | Belcher et al. |
| 2009/0270868 A1 | 10/2009 | Park et al. |
| 2009/0274350 A1 | 11/2009 | Pavlovskaia et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2010/0016947 A1 | 1/2010 | Dobak et al. |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0042105 A1 | 2/2010 | Park et al. |
| 2010/0049195 A1 | 2/2010 | Park et al. |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0168857 A1 | 7/2010 | Hatch |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217109 A1 | 8/2010 | Belcher |

| | | | | | | | |
|---|---|---|---|---|---|---|---|
| 2010/0217270 | A1 | 8/2010 | Polinski et al. | EP | 1938749 | A2 | 7/2008 |
| 2010/0217338 | A1 | 8/2010 | Carroll et al. | EP | 1669033 | B1 | 2/2009 |
| 2010/0228257 | A1 | 9/2010 | Bonutti | FR | 1111677 | | 3/1956 |
| 2010/0249657 | A1 | 9/2010 | Nycz et al. | FR | 2429582 | A1 | 1/1980 |
| 2010/0249796 | A1 | 9/2010 | Nycz | FR | 2659226 | A1 | 9/1991 |
| 2010/0262150 | A1 | 10/2010 | Lian | FR | 2721195 | A1 | 12/1995 |
| 2010/0274253 | A1 | 10/2010 | Ure | FR | 2768916 | A1 | 4/1999 |
| 2010/0281678 | A1 | 11/2010 | Burdulis, Jr. et al. | FR | 2819168 | A1 | 7/2002 |
| 2010/0286700 | A1 | 11/2010 | Snider et al. | GB | 2094590 | A | 9/1982 |
| 2010/0292743 | A1 | 11/2010 | Singhal et al. | GB | 2197790 | A | 6/1988 |
| 2010/0305574 | A1 | 12/2010 | Fitz et al. | GB | 2426200 | A | 11/2006 |
| 2010/0324692 | A1 | 12/2010 | Uthgenannt et al. | GB | 2437003 | A | 10/2007 |
| 2011/0004317 | A1 | 1/2011 | Hacking et al. | GB | 2442441 | A | 4/2008 |
| 2011/0015636 | A1 | 1/2011 | Katrana et al. | JP | 59157715 | A | 9/1984 |
| 2011/0015639 | A1 | 1/2011 | Metzger et al. | JP | 60231208 | A | 11/1985 |
| 2011/0029091 | A1 | 2/2011 | Bojarski et al. | KR | 20050072500 | A | 7/2005 |
| 2011/0029116 | A1 | 2/2011 | Jordan et al. | KR | 20050084024 | A | 8/2005 |
| 2011/0046735 | A1 | 2/2011 | Metzger et al. | RU | 2083179 | C1 | 7/1997 |
| 2011/0054478 | A1 | 3/2011 | Vanasse et al. | RU | 2113182 | C1 | 6/1998 |
| 2011/0066193 | A1 | 3/2011 | Lang et al. | RU | 2125835 | C1 | 2/1999 |
| 2011/0071528 | A1 | 3/2011 | Carson | RU | 2138223 | C1 | 9/1999 |
| 2011/0071529 | A1 | 3/2011 | Carson | RU | 2175534 | C2 | 11/2001 |
| 2011/0071530 | A1 | 3/2011 | Carson | RU | 2187975 | C1 | 8/2002 |
| 2011/0071532 | A1 | 3/2011 | Carson | TW | I231755 | | 5/2005 |
| 2011/0071533 | A1 | 3/2011 | Metzger et al. | WO | 8807840 | A1 | 10/1988 |
| 2011/0092804 | A1 | 4/2011 | Schoenefeld et al. | WO | 8909028 | A1 | 10/1989 |
| 2011/0093086 | A1 | 4/2011 | Witt et al. | WO | 8911257 | A1 | 11/1989 |
| | | | | WO | 9107139 | A1 | 5/1991 |

FOREIGN PATENT DOCUMENTS

| | | | | | | | |
|---|---|---|---|---|---|---|---|
| CA | 2501041 | | 4/2004 | WO | 9325157 | A1 | 12/1993 |
| CA | 2505371 | | 5/2004 | WO | 9413218 | A1 | 6/1994 |
| CA | 2505419 | | 6/2004 | WO | 9528688 | A1 | 10/1995 |
| CA | 2506849 | | 6/2004 | WO | 9607361 | | 3/1996 |
| CA | 2546958 | | 6/2005 | WO | 9729703 | | 8/1997 |
| CA | 2546965 | | 6/2005 | WO | 9732671 | A1 | 9/1997 |
| CA | 2588907 | | 6/2006 | WO | 9800072 | A1 | 1/1998 |
| CA | 2590534 | | 6/2006 | WO | 9832384 | A1 | 7/1998 |
| CH | 117960 | | 5/1927 | WO | 9901073 | A1 | 1/1999 |
| CN | 1630495 | A | 6/2005 | WO | 9932045 | A1 | 7/1999 |
| CN | 1728976 | A | 2/2006 | WO | 9952473 | A1 | 10/1999 |
| CN | 1729483 | A | 2/2006 | WO | 9959106 | A1 | 11/1999 |
| CN | 1729484 | A | 2/2006 | WO | 0170142 | A1 | 9/2001 |
| CN | 1913844 | A | 2/2007 | WO | 0184479 | A1 | 11/2001 |
| CN | 101111197 | A | 1/2008 | WO | 0218019 | | 3/2002 |
| DE | 337437 | | 5/1921 | WO | 0226145 | A2 | 4/2002 |
| DE | 3339259 | C1 | 3/1985 | WO | 0236024 | A1 | 5/2002 |
| DE | 3447365 | A1 | 7/1986 | WO | 02096268 | A2 | 12/2002 |
| DE | 3717871 | C2 | 11/1989 | WO | 03051210 | A2 | 6/2003 |
| DE | 3925488 | A1 | 2/1990 | WO | 03051211 | A1 | 6/2003 |
| DE | 3902249 | A1 | 8/1990 | WO | 04000139 | A1 | 12/2003 |
| DE | 4016704 | C1 | 9/1991 | WO | 2004032806 | A1 | 4/2004 |
| DE | 4219939 | A1 | 12/1993 | WO | 2004017842 | A3 | 6/2004 |
| DE | 04219939 | A1 | 12/1993 | WO | 2004049981 | A2 | 6/2004 |
| DE | 3717871 | C3 | 5/1995 | WO | 2004051301 | A2 | 6/2004 |
| DE | 4219939 | C2 | 10/1995 | WO | 2004075771 | A1 | 9/2004 |
| DE | 4421153 | A1 | 12/1995 | WO | 2004078069 | A2 | 9/2004 |
| EP | 97001 | A1 | 12/1983 | WO | 2004084725 | | 10/2004 |
| EP | 0114505 | A1 | 8/1984 | WO | 2005018453 | A1 | 3/2005 |
| EP | 0326768 | A2 | 8/1989 | WO | 2005051239 | A1 | 6/2005 |
| EP | 337901 | A1 | 10/1989 | WO | 2005051240 | A1 | 6/2005 |
| EP | 0579868 | A2 | 1/1994 | WO | 2005053564 | A2 | 6/2005 |
| EP | 0650706 | A1 | 5/1995 | WO | 2005077039 | A2 | 8/2005 |
| EP | 756735 | B1 | 8/1998 | WO | 2005084558 | A1 | 9/2005 |
| EP | 0908836 | A3 | 1/1999 | WO | 2005099636 | A1 | 10/2005 |
| EP | 0908836 | A2 | 4/1999 | WO | 2006058057 | A2 | 6/2006 |
| EP | 0916324 | A2 | 5/1999 | WO | 2006060795 | A1 | 6/2006 |
| EP | 904158 | A4 | 6/1999 | WO | 2006058057 | A8 | 7/2006 |
| EP | 1013231 | A2 | 6/2000 | WO | 2006092600 | A1 | 9/2006 |
| EP | 1013231 | A3 | 8/2000 | WO | 2006127486 | A2 | 11/2006 |
| EP | 1136041 | A2 | 9/2001 | WO | 2006134345 | A1 | 12/2006 |
| EP | 904158 | B1 | 7/2002 | WO | 2007041375 | A2 | 4/2007 |
| EP | 1321107 | A1 | 6/2003 | WO | 2007053572 | A2 | 5/2007 |
| EP | 709061 | B1 | 7/2003 | WO | 2007062079 | A2 | 5/2007 |
| EP | 1136041 | A3 | 10/2003 | WO | 2007092841 | A2 | 8/2007 |
| EP | 1348393 | A1 | 10/2003 | WO | 2007097853 | A2 | 8/2007 |
| EP | 1437102 | A1 | 7/2004 | WO | 2007097854 | A2 | 8/2007 |
| EP | 1486900 | A1 | 12/2004 | WO | 2007097853 | A3 | 12/2007 |
| EP | 1498851 | A1 | 1/2005 | WO | 2007137327 | A1 | 12/2007 |
| EP | 1444957 | B1 | 3/2007 | WO | 2007145937 | A2 | 12/2007 |
| | | | | WO | 2007145937 | A3 | 2/2008 |

| WO | 2008014618 A1 | 2/2008 |
| WO | 2008021494 A2 | 2/2008 |
| WO | 2008040961 A1 | 4/2008 |
| WO | 2008044055 A1 | 4/2008 |
| WO | 2008101090 A2 | 8/2008 |
| WO | 2008112996 A1 | 9/2008 |
| WO | 2008117028 A1 | 10/2008 |
| WO | 2008140748 A1 | 11/2008 |
| WO | 2009001083 A1 | 12/2008 |
| WO | 2009025783 A1 | 2/2009 |
| WO | 2009045960 A1 | 4/2009 |
| WO | 2009129063 A1 | 10/2009 |
| WO | 2009129067 A1 | 10/2009 |
| WO | 2010033431 A1 | 3/2010 |

OTHER PUBLICATIONS van den Dikkenberg et al., "Measuring functional abilities of patients with knee problems; rationale and construction of the DynaPort knee test," Knee Surgery, Sports Traumatology, Arthroscopy, vol. 10, pp. 204-212.

Patterson et al., "Automated physical activity monitoring: validation and comparison with physiological and self-report measures," Psychophysiology, 1993, vol. 30, pp. 296-305.

Xsens Motion Technologies. "Xbus Master: Portable multi-sensor system." [Online] Publication date unknown. <http://www.xsens.com/index.php?mainmenu=products&submenu=human_motion&subsubmenu=Xbus_Master>.

Xsens Motion Technologies. "MTx: 3DOF Orientation Tracker." [Online] Publication date unknown. <http://www.xsens.com/index.php?mainmenu=products&submenu=human_motion&subsubmenu=MTx>.

Xsens Motion Technologies. "Moven—inertial motion capturing." [Online] Publication date unknown. <http://www.xsens.com/index.php?mainmenu=products&submenu=human_motion&subsubmenu=Moven>.

Radermacher et al., "Computer Assisted Orthopaedic Surgery with Image Based Individual Templates," Clin Orthopaedics and Related Research, 354, 28-38, 1998.

Hafez et al., "Computer-assisted Total Knee Arthroplasty Using Patient-specific Templating," Clin Orthopaedics and Related Research, 444, 184-192, 2006.

Berry, Seedhom, et al., "Personalised image-based templates for intra-operative guidance," Proceedings of the Institution of Mechanical Engineers, Part H: Journal of Engineering in Medicine, 111-118, 2005.

SurgiTAIX AG, "OrthoTAIX for Orthopaedic Surgery." Available at http://www.surgitaix.com/Products/OrthoTAIX/OrthoTAIX.pdf.

Radermacher et al., "Computer-Integrated Orthopaedic Surgery: Connection of Planning and Execution in Surgical Intervention," Computer Integrated Surgery, 451-463, 1995.

Radermacher et al., "CT Image-Based Planning and Execution of Interventions in Orthopedic Surgery Using Individual Templates—Experimental Results and Aspects of Clinical Applications," Computer Assisted Orthopaedic Surgery, L.P. Nolte and R. Ganz, eds, 42-52, Hogrefe & Huber Publishing 1999.

Accuracy of CT-Based Patient Specific Total Knee Arthroplasty Instruments; AAHKS 20th Annual Meeting, Submission Record, Submission ID # 4177, Apr. 14, 2010.

European Search Report; European Patent Application No. 08165418.8-2165; dated Jan. 23, 2009; 6 pages.

Hube et al.; Orthopaedic Surgery The Essentials, Chaper 36 Knee Reconstruction; 1999; 12 pages.

Corin Medical Limited; The Corin X-ActTM Instrumentation and Operative Technique; Nov. 1998; 9 pages.

Kraus et al.; A Comparative Assessment of Alignment Angle of the Knee by Radiographic and Physical Examination Methods; Jun. 6, 2005; 6 pages.

Depuy; LCS Total Knee System—Surgical Procedure; 1989; 36 pages.

Engh et al.; Legent II Surgical Technique; The Concept of Personalization—Total Knee Replacement Using the AMK—Legend II; 1992; 31 pages.

Lotke; Knee Arthroplasty; Primary Total Knees—Standard Principles and Techniques; Raven Press, Ltd.; 5 pages; 1995.

Mills et al.; Use of Computer Tomographic Reconstruction in Planning Osteotomies of the Hip; Jan. 1992; 6 pages.

Portheine et al.; Development of a clinical demonstrator fro computer assisted orthopedic surgery with CT-image based individual templates; 1997; 6 pages.

Radermacher et al.; Image Guided Orthopedic Surgery Using Individual Templates; 10 pages.

Radermacher et al.; Computer Assisted Matching of Planning and Execution in Orthopedic Surgery; 1993; 2 pages.

Radermacher et al.; Technique for Better Execution of CT Scan Planned Orthopedic Surgery on Bone Structures; 9 pages.

* cited by examiner

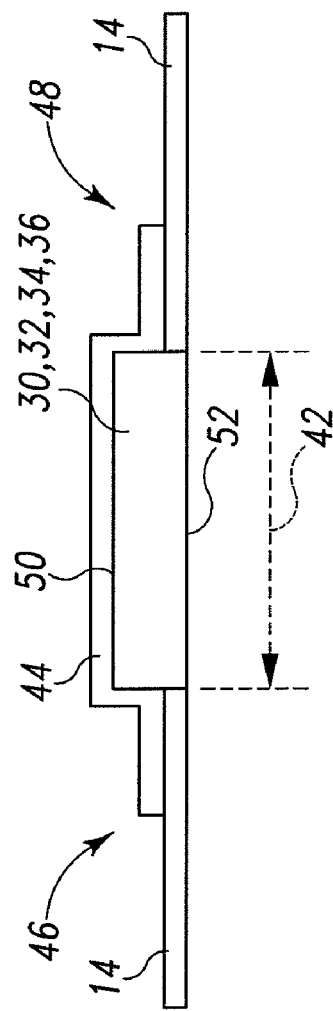

METHOD AND SYSTEM FOR DESIGNING PATIENT-SPECIFIC ORTHOPAEDIC SURGICAL INSTRUMENTS

CROSS-REFERENCE

Cross-reference is made to U.S. Utility patent application Ser. No. 11/616,456 entitled "Apparatus, System, and Method for Monitoring the Range of Motion of a Patient's Joint," which was filed on Dec. 27, 2006 by Sherrod A. Woods et al., the entirety of which is expressly incorporated herein by reference.

TECHNICAL FIELD

The present disclosure relates generally to methods, devices, and systems for designing patient-specific orthopaedic surgical instruments.

BACKGROUND

Joint arthroplasty is a well-known surgical procedure by which a diseased and/or damaged natural joint is replaced by a prosthetic joint. A typical knee prosthesis includes a tibial tray, a femoral component, and a polymer insert or bearing positioned between the tibial tray and the femoral component. To facilitate the replacement of the natural joint with the knee prosthesis, orthopaedic surgeons use a variety of orthopaedic surgical instruments such as, for example, cutting blocks, drill guides, milling guides, and other surgical instruments. Typically, the orthopaedic surgical instruments are generic with respect to the patient such that the same orthopaedic surgical instrument may be used on a number of different patients during similar orthopaedic surgical procedures.

SUMMARY

According to one aspect, a method for designing a patient-specific orthopaedic surgical instrument to be used on a knee of the patient may include coupling a knee sleeve to a leg of the patient. The knee sleeve may include a first sensor and a second sensor. The first sensor may be coupled to a superior half of the knee sleeve. The first sensor may generate first data indicative of the position of the first sensor. The second sensor may be coupled an inferior half of the knee sleeve. The second sensor may generate second data indicative of the position of the second sensor.

The method may also include determining angulation data indicative of the angulation of the knee of the patient based on the first data and the second data. The angulation data may be indicative of, for example, the ligament laxity of the knee. In some embodiments, determining the angulation data may include determining valgus data indicative of an amount of valgus angulation of the leg of the patient and determining varus data indicative of an amount of varus angulation of the leg of the patient. The valgus data may be indicative of the amount of valgus angulation of the leg of the patient with respect to a first amount of force applied to the leg at a first location on the leg. Similarly, the varus data may be the indicative of the amount of varus angulation of the leg of the patient with respect to a second amount of force applied to the leg at a second location on the leg. Additionally or alternatively, determining the angulation data may include determining the position of the femur of the leg of the patient based on the first data and determining the position of the tibia of the leg of the patient based on the second data.

In some embodiments, the angulation data may be determined by applying an amount of force to the leg of the patient at a location on the leg to position the leg of the patient in a valgus position. Angle data indicative of the valgus angulation of the leg when in the valgus position may be generated. Additionally, force data indicative of the amount of force may be generated. Further, location data indicative of the location on the leg at which the force is applied relative to a predetermined location may also be generated. Additionally or alternatively, the angulation data may be determined by applying an amount of force to the leg of the patient at a location on the leg to position the leg of the patient in a varus position. Angle data indicative of the varus angulation of the leg when in the varus position may be generated. Additionally, force data indicative of the amount of force may be generated. Further location data indicative of the location on the leg at which the force is applied relative to a predetermined location may also be generated.

The method may also include generating a medical image of the knee of the patient. The medical images may be embodied as, for example, computed tomography (CT) images and/or magnetic resonance imaging (MRI) images. The method may also include generating a three dimensional image of the knee of the patient based on the medical images.

The method may further include determining a design of a patient-specific orthopaedic surgical instrument based on the medical image and the angulation data. In some embodiments, the patient-specific orthopaedic surgical instrument may include a bone-contacting surface having a negative contour matched to the contour of a portion of the patient's bone. Additionally or alternatively, the patient-specific orthopaedic surgical instrument may be embodied as a bone-cutting block having a cutting guide defined in the cutting block at a location determined based on the angulation data. Additionally or alternatively, in other embodiments, the patient-specific orthopaedic surgical instrument may be embodied as a bone-cutting block configured to be coupled to the bone of the patient. In some embodiments, the method may also include determining constraint data indicative of preferences of an orthopaedic surgeon. In such embodiments, the patient-specific orthopaedic surgical instrument may be designed based on the medical image, the angulation data, and the constraint data.

According to another aspect, a system for designing a patient-specific orthopaedic surgical to be used a knee of a patient may include a knee sleeve configured to be coupled to a leg of the patient, a first sensor coupled to the knee sleeve, and a second sensor coupled to the knee sleeve. The first sensor may be configured to generate first data indicative of the position of the first sensor and the second sensor may be configured to generate second data indicative of the position of the second sensor. The system may also include a force sensor. The force sensor may be configured to generate force data indicative of an amount of force applied to the leg of the patient. In some embodiments, the force sensor may be incorporated into a glove wearable by an orthopaedic surgeon. In other embodiments, the force sensor may be coupled to the knee sleeve.

The system may also include a first computer. The first computer may be configured to determine angle data indicative of the degree of angulation between the femur and the tibia based on the first data and the second data. Additionally or alternatively, the first computer may be configured to determine location data indicative of the location of the force sensor relative to a predetermined location. Additionally or alternatively, the first computer may be configured to store the angle data, force data, and location data. In some embodiments, the first computer may also be configured to determine third data indicative of the position of the femur of the leg of the patient based on the first data and to determine fourth data indicative of the position of the tibia of the leg of the patient.

The system may also include a second computer in some embodiments. The second computer may be remote from the first computer. The second computer may be configured to generate a three-dimensional model of the customized patient orthopaedic surgical instrument based on the angle data, force data, and location data According to a further aspect, a method for designing a patient-specific orthopaedic surgical may include coupling a knee sleeve to a leg of the patient. The knee sleeve may include a first sensor coupled to a superior half of the knee sleeve and a second sensor coupled to an inferior half of the knee sleeve. The first sensor may generate first data indicative of the position of the first sensor and the second sensor may generate second data indicative of the position of the second sensor.

The method may also include generating laxity data indicative of the ligament laxity of the knee of the patient based on the first and second data. The method may also include generating a design of a patient-specific orthopaedic surgical instrument based on the laxity data. In some embodiments, the method may also include generating a medical image of the knee of the patient. In such embodiments, the patient-specific orthopaedic surgical instrument is designed based on the laxity data and the medical image.

In some embodiments, the laxity data may be generated by, for example, applying a first amount of force to the leg at a first location on the leg to position the leg of the patient in a valgus position, generating first angle data indicative of the valgus angulation of the leg when in the valgus position, generating first force data indicative of the first amount of force, and generating first location data indicative of the first location relative to a predetermined location. Additionally or alternatively, the laxity data may be generated by applying a second amount of force to the leg at a second location on the leg to position the leg of the patient in a varus position, generating second angle data indicative of the varus angulation of the leg when in the varus position, generating second force data indicative of the second amount of force, generating second location data indicative of the second location relative to the predetermined location. In such embodiments, the orthopaedic surgical instrument may be designed based on the first angle data, the first force data, the first location data, the second angle data, the second force data, and the second location data.

BRIEF DESCRIPTION OF THE DRAWINGS

The detailed description particularly refers to the following figures, in which:

FIG. 3 is a cross-sectional view of one embodiment of a knee sleeve of the apparatus of FIG. 1;

FIG. 4 is a cross-sectional view of another embodiment of the knee sleeve of the apparatus of FIG. 1;

DETAILED DESCRIPTION OF THE DRAWINGS

Figure 1:
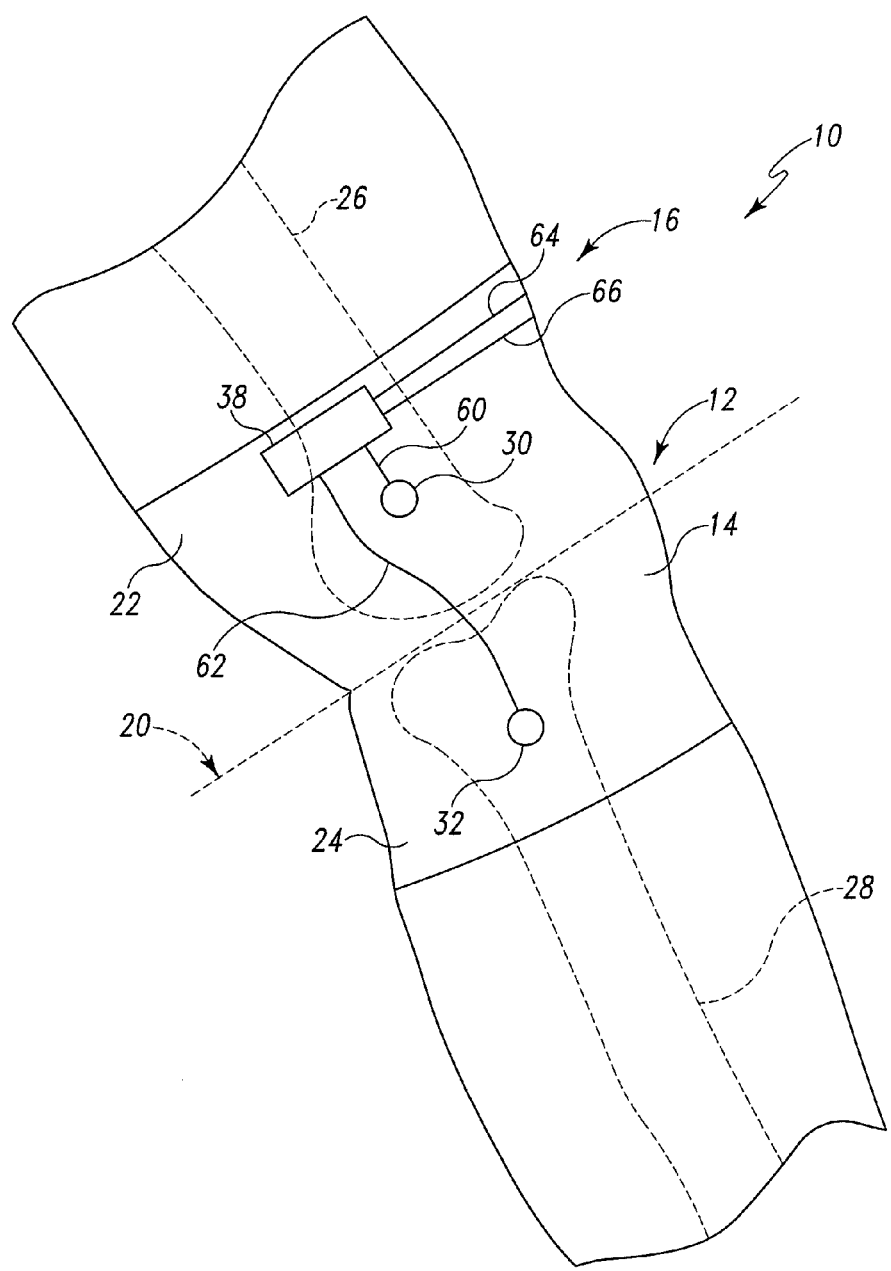
FIG. 1 is a lateral elevation view of one embodiment of an apparatus for determining the angulation of a patient's knee.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, an apparatus 10 for determining the range of motion and/or angulation of a patient's knee 12 includes a knee sleeve 14 and sensing circuitry 16 coupled to the knee sleeve 14. The knee sleeve 14 includes a superior half 22 and an inferior half 24 defined by a bisecting plane 20. The knee sleeve 14 has a substantially cylindrical shape having an opening at each end and an inner cavity defined therebetween through which the leg of the patient is inserted when the knee sleeve 14 is worn by the patient.

As illustrated in FIG. 1, when the knee sleeve 14 is worn by the patient, the superior half 22 of the knee sleeve covers a portion of the distal end of the patient's femur 26 and the inferior half 24 covers a portion of the proximal end of the patient's tibia 28. The knee sleeve 14 may be formed from any flexible material that allows the patient to move the knee joint 12 between a flexion position and an extension position. For example, the knee sleeve 14 may be formed from a stretchable, form-fitting textile such as a neoprene material, nylon, a spandex material such as Lycra™, or the like. Additionally, in some embodiments, the knee sleeve 14 may be formed from a sterilized material such that the knee sleeve 14 may be worn by the patient soon after the surgical procedure and/or during post-surgery recovery.

The knee sleeve 14 may be sized based on one or more parameters such as the physical size of the patient. For example, the knee sleeve 14 is sized such that the knee sleeve 14 covers only the knee joint region of the patient's leg. That is, when the knee sleeve 14 is worn by the patient, the superior half 22 of the knee sleeve 14 does not extend up to the groin region of the patient and the inferior half 24 does not extend down to the ankle region of the patient. Because the knee sleeve 14 is worn only around the knee joint region of the patient's leg, the natural movement of the patient's joint is not substantially affected by the use of the knee sleeve 14 unlike a full-leg sleeve or full body suit, which extends from groin-to-ankle. Although the knee sleeve 14 does not substantially affect the natural movement of the patient's joint, the knee sleeve 14 may provide some amount of additional support to the knee joint in some embodiments.

In the illustrative embodiment, the sensing circuitry 16 includes a number of sensor circuits 30, 32, 34, 36 and a communication circuit 38. In some embodiments, the sensor circuits 30, 32, 34, 36 and the communication circuit 38 are incorporated into the knee sleeve 14. For example, the circuits 30, 32, 34, 36, 38 may be woven into the material forming the knee sleeve 14 or otherwise attached to the knee sleeve 14 in a non-removable manner using, for example, a permanent adhesive or the like.

Alternatively, in other embodiments, the sensor circuits 30, 32, 34, 36 and the communication circuit 38 may be removably attached to the knee sleeve 14. For example, as illustrated in FIG. 3, the sensor circuits 30, 32, 34, 36 and/or the communication circuit 38 may be removably attached to the knee sleeve 14 using an attaching member 40, such as a hook-and-loop material or other non-permanent adhesive. In such embodiments, the attaching member 40, or a portion thereof, may be secured to a housing (see FIG. 6) of the circuit 30, 32, 34, 36, 38. In use, the sensor circuits 30, 32, 34, 36 and/or the communication circuit 38 may be attached to the knee sleeve 14 by pressing the attaching member 40 onto the knee sleeve 14. In such embodiments, the sensor circuits 30, 32, 34, 36 and the communication circuit 38 may be coupled to the knee sleeve 14 during use and decoupled therefrom when not in use. Additionally, in embodiments wherein the circuits 30, 32, 34, 36, 38 are removable from the knee sleeve 14, the circuits 30, 32, 34, 36, 38 may be reusable while the knee sleeve 14 is disposed of after each use or otherwise periodically.

In some embodiments, as illustrated in FIG. 4, the knee sleeve may include a number of apertures 42. The apertures 42 are sized to receive at least a portion of one of the sensor circuits 30, 32, 34, 36. That is, when the sensor circuit 30, 32, 34, 36 is coupled to the knee sleeve 14, a portion of the sensor circuit 30, 32, 34, 36 is positioned in the aperture 42. The sensor circuit 30, 32, 34, 36 is held in place via an attaching member 44, which wraps over the sensor circuit 30, 32, 34, 36 and contacts a portion of the knee sleeve 14 at distal ends 46, 48. The attaching member 44 may be similar to the attaching member 40 described above in regard to FIG. 3. For example, the attaching member 44 may be secured to a top surface 50 of the sensor circuit 30, 32, 34, 36 and formed from a hook-and-loop material.

When the sensor circuit 30, 32, 34, 36 is positioned in the aperture 42, a bottom surface 52 of the sensor circuit 30, 32, 34, 36 may be positioned in contact with the skin of the patient. The knee sleeve 14 may include any number of apertures 42. In one particular embodiment, the knee sleeve 14 includes one aperture 42 for each sensor circuit 30, 32, 34, 36. Additionally, the apertures 42 may be defined in knee sleeve 14 in predetermined locations such that the sensor circuits 30, 32, 34, 36 are similarly located when coupled thereto. For example, as discussed in more detail below, one or more apertures 42 may be defined on a lateral side of the knee sleeve 14 and one or more additional apertures 42 may be defined on the anterior side of the knee sleeve 14.

Figure 2:
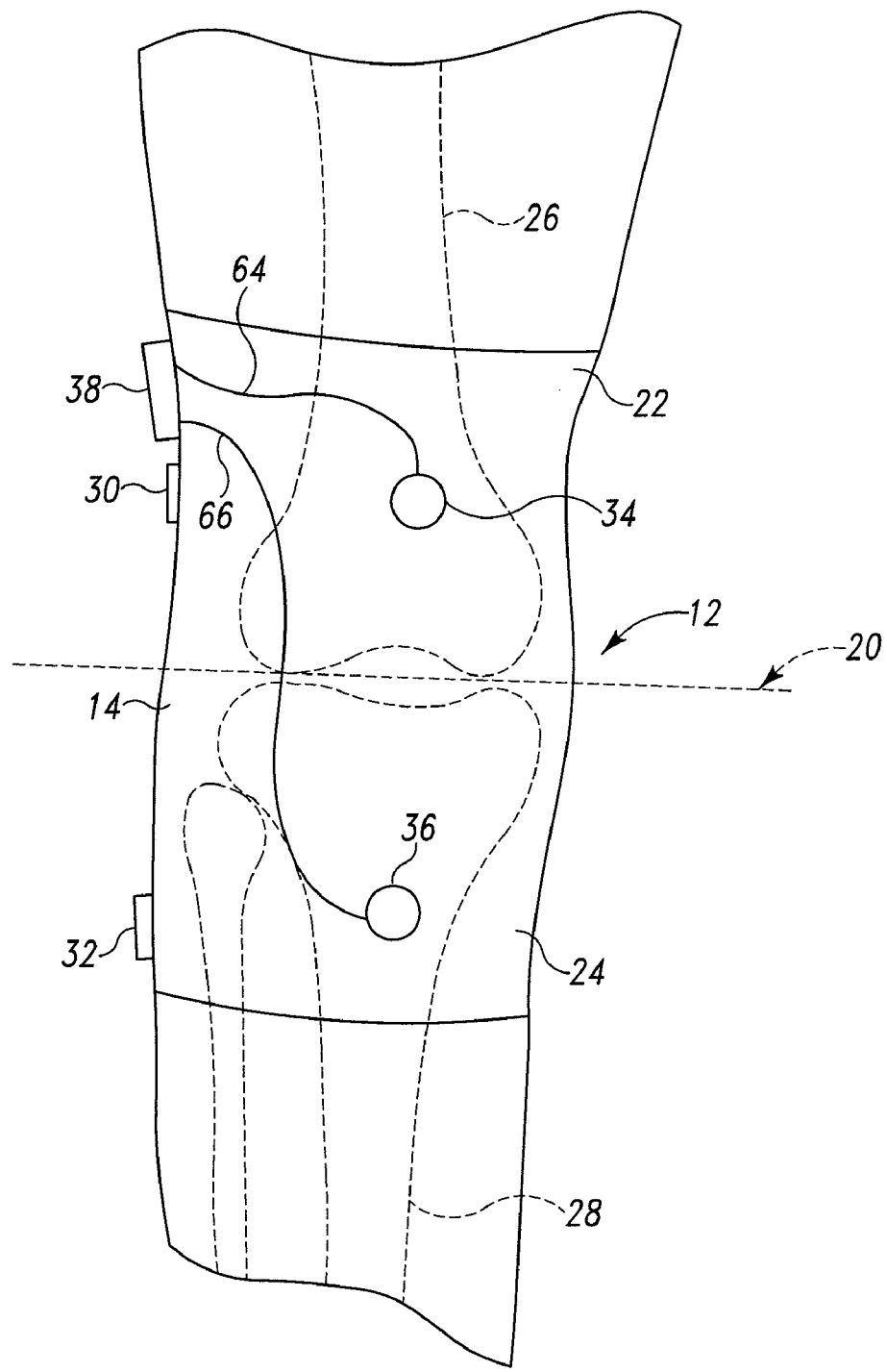
FIG. 2 is an anterior elevation view of the apparatus of FIG. 1.

Referring back to FIGS. 1 and 2, the sensor circuits 30, 32, 34, 36 are positioned on the knee sleeve 14 such that one or more of the sensor circuits 30, 32, 34, 36 is located on each side (i.e., the superior and inferior sides) of the knee joint 12 of the patient. In particular, sensor circuit 30 is coupled on the lateral side of the superior half 22 of the knee sleeve 12 and the sensor circuit 32 is coupled on the lateral side of the inferior half 24 of the knee sleeve as illustrated in FIG. 1. Additionally, as illustrated in FIG. 2, the sensor circuit 34 is coupled on the anterior side of the superior half 22 of the knee sleeve 12 and the sensor circuit 36 is coupled on the anterior side of the inferior half 24 of the knee sleeve 12. Although the illustrative apparatus 10 includes four sensor circuits, it should be appreciated that in other embodiments a greater or lesser number of sensor circuits may be used. For example, in some embodiments, only two sensor circuits are used and each sensor circuit is positioned on one side of the knee joint 12 (e.g., similar to sensor circuits 30, 32). However, by using additional sensor circuits, such as sensor circuits 34, 36, an amount of redundancy and an improvement in measurement accuracy may be achieved with the apparatus 10.

In the illustrative embodiment, the sensor circuits 30, 34 and the sensor circuits 32, 36 are positioned on the lateral and anterior side of the knee sleeve 14 to reduce the likelihood that any one of the sensor circuits 30, 32, 34, 36 obstructs the normal movement of the patient or becomes dislodged from the knee sleeve 14. For example, such positioning of the sensor circuits 30, 32, 34, 36 may reduce the likelihood that the sensor circuits 30, 32, 34, 36 inadvertently become dislodged from the knee sleeve 14 by movement of the patient from, for example, being repeatedly hit or rubbed by the leg of the patient as may be the case if sensor circuits were located on the medial side of the knee sleeve 14. However, in other embodiments, the sensor circuits 30, 34 and 32, 36 may be positioned in other locations on the knee sleeve 14.

Figure 5:
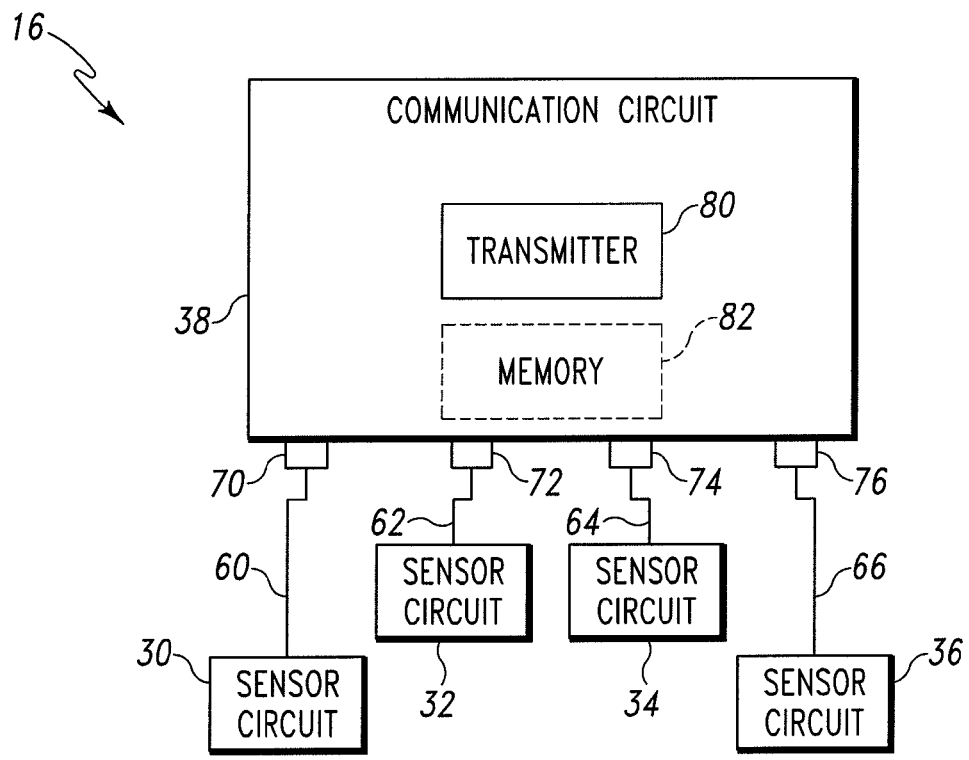
FIG. 5 is a simplified block diagram of one embodiment of the sensing circuitry of the apparatus of FIG. 1.

Each of the sensor circuits 30, 32, 34, 36 is electrically coupled to the communication circuit 38 via a number of communication links 60, 62, 64, 66, respectively. The communication links 60, 62, 64, 66 may be embodied as any type of communication link capable of providing electrical communication between the sensor circuits 30, 32, 34, 36 and the communication circuit 38. For example, the communication links 60, 62, 64, 66 may be embodied as any number of wires, cables, fiber optic cables, and/or the like. In some embodiments, the sensor circuits 30, 32, 34, 36 may be removably coupled to the communication circuit 38. For example, as illustrated in FIG. 5, the sensor circuits 30, 32, 34, 36 may be communicatively coupled to the communication circuit 38 via connectors 70, 72, 74, 76. In this way, individual sensor circuits that become damaged over time may be replaced without the requirement of replacing the communication circuit 38. In addition, only those sensor circuits required for the particular application or implementation may be coupled to the communication circuit 38. For example, in those embodiments including only two sensor circuits rather than four, the sensor circuits 30, 32 may be coupled to the communication circuit 38 and to the knee sleeve 14, while the sensor circuits 34 and 36 are decoupled from the communication circuit 38 and removed.

As illustrated in FIG. 5, the communication circuit 38 includes a transmitter 80. The transmitter 80 is configured to receive the sensor data signals from the sensor circuits 30, 32, 34, 36 and transmit the sensor data signals to a receiver such as a remote computer as discussed below in more detail in regard to FIG. 7. The transmitter 80 may be embodied as any transmitter circuitry capable of wirelessly transmitting the data signals received from the sensor circuits 30, 32, 34, 36. The transmitter 80 is sized to allow the communication circuit 38 to be coupled to or incorporated in the knee sleeve 14 while not falling off due to gravity or use or otherwise causing the knee sleeve 14 to become improperly positioned during use. In some embodiments, the communication circuit 38 also includes a memory device 82. The memory device 82 may be embodied as any type of memory device such as, for example, a random access memory (RAM) device. In such embodiments, the transmitter 80 or associated circuitry may be configured to store the sensor data received from the sensor circuits 30, 32, 34, 36 in the memory device 82. In addition, the transmitter 80 or associated circuitry may be configured to retrieve stored sensor data from the memory device 82 and transmit the stored sensor data to a receiver such as a remote computer.

Although the communication circuit 38 is illustrated in FIG. 5 as a single circuit, in some embodiments, the communication circuit 38 may be embodied as any number of transmitters similar to transmitter 80, which may or may not be communicatively coupled to each. In such embodiments, each transmitter may be electrically coupled to a respective one of the sensor circuits 30, 32, 34, 36 and may further form a portion of the respective sensor circuit 30, 32, 34, 36 in some embodiments. For example, in one particular embodiment, the communication circuit 38 is formed from a first transmitter electrically coupled to the sensor circuit 30, a second transmitter electrically coupled to the sensor circuit 32, a third transmitter electrically coupled to the sensor circuit 34, and a fourth transmitter electrically coupled to the sensor circuit 36. Additionally, in such embodiments, any one or more of the sensor circuits 30, 32, 34, 36 may include a memory device similar to memory device 82.

Figure 6:
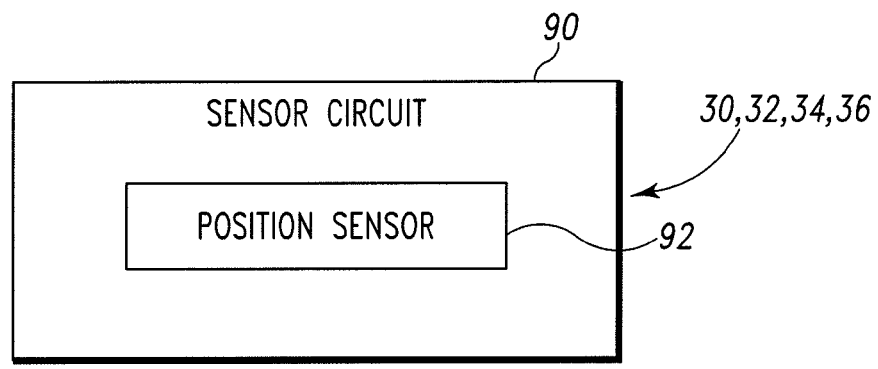
FIG. 6 is a simplified block diagram of one embodiment of a sensor circuit of the sensing circuitry of FIG. 3.

Referring now to FIG. 6, each of the sensor circuits 30, 32, 34, 36 includes a housing 90 and a position sensor 92. The housing 90 may be formed from any material capable of supporting the position sensor 92 and associated circuitry and being coupled to the knee sleeve 14. In one particular embodiment, the housing 90 is formed from a plastic material, but other materials may be used in other embodiments. In embodiments wherein the knee sleeve 14 includes apertures 42, the housing 90 or a portion thereof is sized to be positioned in one of the apertures 42. The position sensor 92 may be embodied as any sensor capable of generating sensor data indicative of the position of the sensor 92. As used herein, the term "position" is intended to mean the spatial location of an object (e.g., the sensor 92) relative to a reference point and/or the spatial orientation of an object (e.g., the sensor 92) relative to a reference axis. For example, in one particular embodiment, the position sensor 92 may be embodied as a microelectromechanical system (MEMS) sensor, such as an accelerometer, configured to generate sensor data indicative of the orientation of the position sensor 92 with respect to the Earth's gravitational field. However, in other embodiments, the position sensor 92 may be embodied as any other type of position sensor, such as optical and/or magnetic position sensors, configured to generate data indicative of the location and/or the orientation of the sensor from which the position of an associated bone of the patient may be determined as described in more detail below in regard to FIG. 10.

Figure 7:
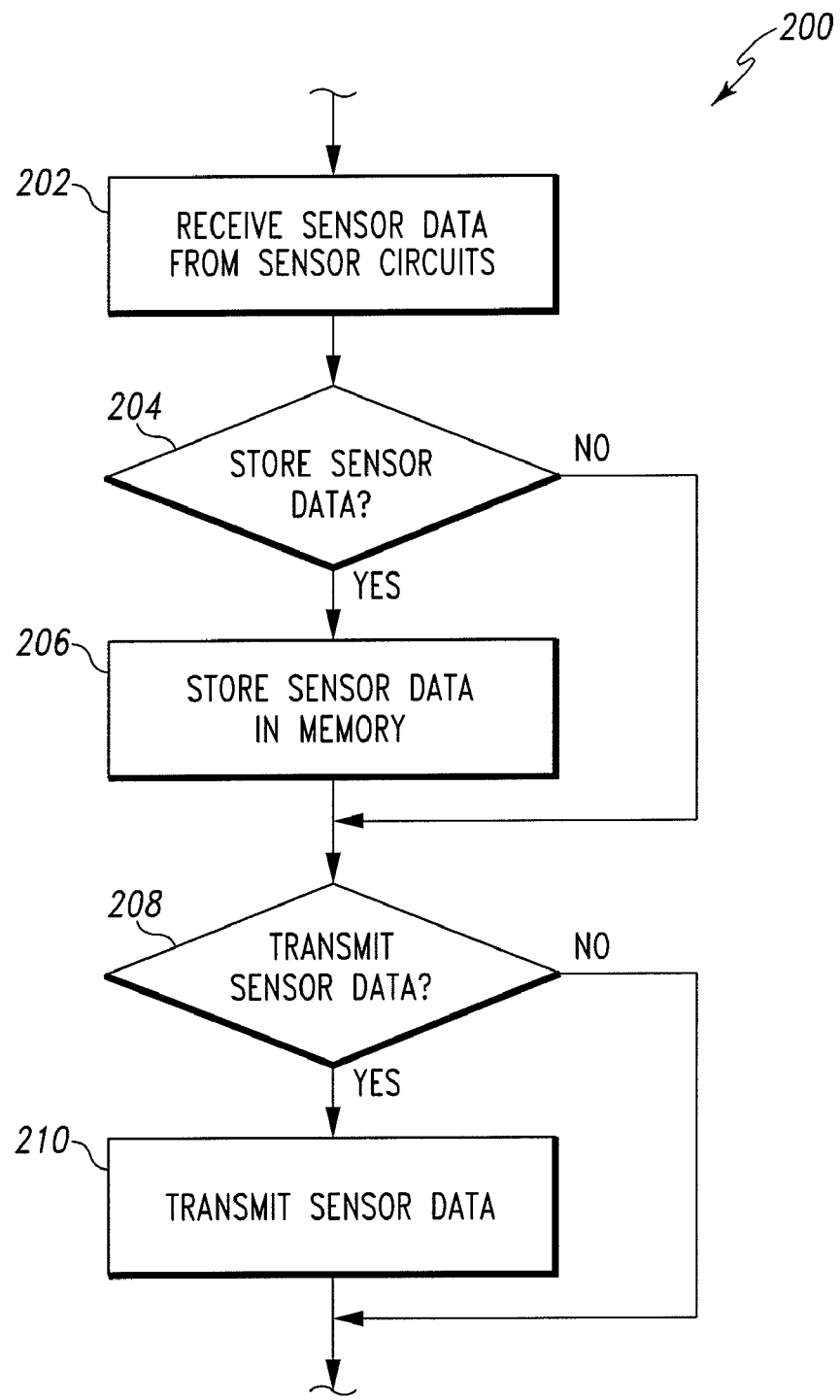
FIG. 7 is a simplified flow diagram of an algorithm for transmitting sensor data, which may be executed by the communication circuit of the system of FIG. 5.

Referring now to FIG. 7, an algorithm 200 for transmitting sensor data that may be executed by the sensing circuitry 16 of the knee sleeve 14 begins with a process step 202. In process step 202, the communication circuitry 38 of the sensing circuit 16 receives sensor data from each of the sensor circuits 30, 32, 34, 36. The communication circuitry 38 may continually, periodically, or selectively receive the sensor data from the sensor circuits 30, 32, 34, 36. For example, the communication circuitry 38 or associated circuitry may be configured to poll the sensor circuits 30, 32, 34, 36 periodically to receive the sensor data. Alternatively, the communication circuit may transmit a signal to each of the sensor circuits 30, 32, 34, 36 to request that the individual sensor circuit 30, 32, 34, 36 transmit the sensor data. Regardless, the communication circuit 38 receives the sensor data in process step 202.

In process step 204, the communication circuit 38 determines whether the sensor data should be stored. If so, the sensor data received from the sensor circuits 30, 32, 34, 36 is stored in the memory device 82 in process step 206. Subsequently or if the sensor data is to be stored, the algorithm 200 advances to process step 208. In process step 208, the communication circuit 38 determines whether the sensor data should be transmitted. The communication circuit 38 may be configured to transmit the data continually, periodically, or in response to a request signal (e.g., a request signal received from the healthcare provider computer 502 described below in regard to FIG. 8) For example, in some embodiments, the communication circuit 38 is configured to transmit the sensor data only during predetermined time periods. In other embodiments, the communication circuit 38 may be configured to transmit the sensor data only after receiving a request for the sensor data from the patient computer 102. Regardless, if the communication circuit 38 determines that the sensor data should be transmitted, the algorithm 200 advances to process step 210 wherein the communication circuit 38 transmits the sensor data to the patient computer 102 via the communication link 106 (or to the healthcare provider computer 104 via the communication link 134). Additionally, in some embodiments such as in those embodiments wherein the communication circuit 38 is configured to store received sensor data, the communication circuit 38 may retrieve the stored sensor data and transmit the stored sensor data in process step 210.

Referring now to FIGS. 8-13, the knee sleeve 14 may be used in a system 500 for determining a design of a patient-specific orthopaedic surgical instrument. As discussed in more detail below in regard to FIG. 13, a patient-specific orthopaedic surgical instrument is an orthopaedic surgical instrument intended for use with a particular patient unlike typical orthopaedic surgical instruments, which are intended for use with a variety of patients.

In some embodiments, the patient-specific orthopaedic surgical instrument may be customized to the particular patient based on the location at which the instrument is coupled to one or more bones, such as the femur and/or tibia, of the patient. For example, in some embodiments, the patient-specific orthopaedic surgical instrument may include a bone-contacting surface having a negative contour that matches the contour of a portion of the bone of the patient. As such, the patient-specific orthopaedic surgical instrument is configured to be coupled to the bone of the patient in a unique location and position with respect to the bone. That is, the negative contour of the bone-contacting surface is configured to receive the matching contour surface of the patient's bone. As such, the orthopaedic surgeon's guesswork and/or intraoperative decision-making with respect to the placement of the orthopaedic surgical instrument may be reduced. For example, the orthopaedic surgeon may not be required to locate landmarks of the patients bone to facilitate the placement of the orthopaedic surgical instrument. Rather, the orthopaedic surgeon may simply couple the patient-specific orthopaedic surgical instrument on the bone or bones of the patient in the unique location. When so coupled, the cutting plane, drilling holes, milling holes, and/or other guides are defined in the a predetermined location because the position of the patient-specific orthopaedic surgical instrument relative to the bone(s) of the patient has been predetermined. The patient-specific orthopaedic surgical instrument may be embodied as any type of orthopaedic surgical instrument such as, for example, a bone cutting block, a drilling guide, a milling guide, or other type of orthopaedic surgical instrument configured to be coupled to a bone of a patient.

Figure 8:
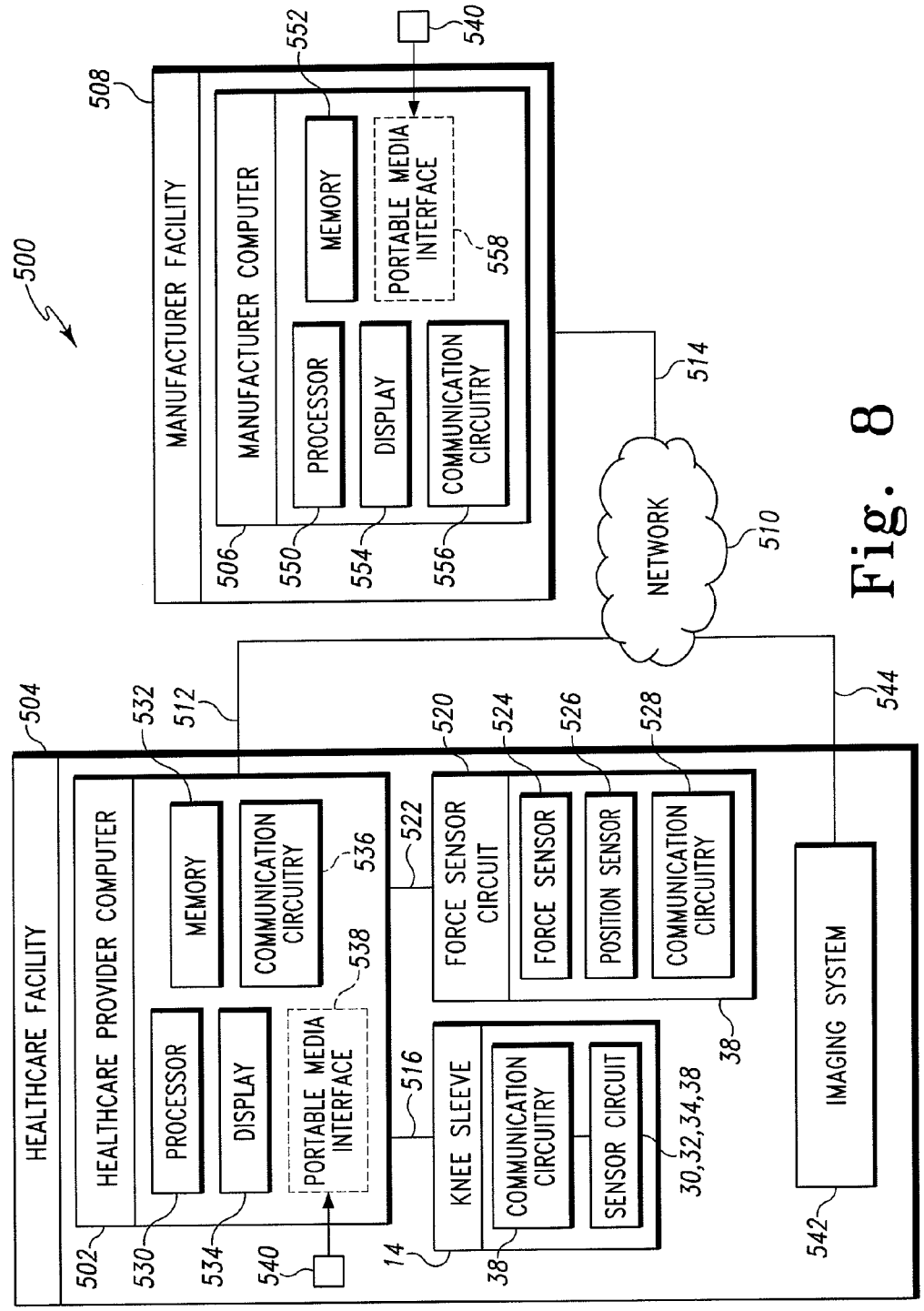
FIG. 8 is a simplified block diagram of a system for designing a patient-specific orthopaedic surgical instrument.

Referring to FIG. 8, the system 500 includes a healthcare provider computer 502 located in a healthcare facility 504 such as a hospital facility or the office of the orthopaedic surgeon. The system 500 also includes a manufacturer computer 506 located in the facility of a manufacturer or vendor of patient-specific orthopedic surgical instruments. The healthcare provider computer 502 is communicatively coupled to the manufacture computer 506 via a network 510. The network 510 may be embodied as any type of communication network capable of facilitating communication between the healthcare provider computer 502 and the manufacturer computer 506. For example, the network 510 may be embodied as a wide area network (WAN), a local area network (LAN), or form a portion of a publicly-accessible, global network such as, for example, the Internet. In addition, the network 510 may be a wired network, a wireless network, or a combination thereof. As such, the network 510 may include any number of devices for providing communication between the computers 502, 506 such as routers, switches, hubs, computers, communication links, and the like.

The healthcare provider computer 502 is coupled to the network 510 via a number of communication links 512. Similarly, the manufacturer computer 506 is coupled to the network 510 via a number of communication links 514. The communication links 512, 514 may be embodied as any type of communication links capable of providing communication between the healthcare provider computer 502 and the manufacturer computer 506. For example, the communication links 512, 514 may be embodied as any number of cables, wires, fiber optic cables, wireless signals, and/or the like.

The healthcare provider computer 502 is also communicatively coupled to the knee sleeve 14 (e.g., the communication circuitry 38 of the knee sleeve 14) via a number of communication links 516. The communication links 516 may be embodied as any type of communication links capable of facilitating communication between the sensing circuit 16 of the knee sleeve 14 and the healthcare provider computer 502. For example, the communication links 516 may be embodied as any number of cables, wires, fiber optic cables, wireless signals, and/or the like. The healthcare provider computer 502 is also communicatively coupled to a force sensor circuit 520 via a number of communication links 522. Similar to the communication links 516, the communication links 522 may be embodied as any type of communication links capable of facilitating communication between the force sensor circuit 520 and the healthcare provider computer 502. For example, the communication links 522 may be embodied as any number of cables, wires, fiber optic cables, wireless signals, and/or the like.

The force sensor circuit 520 includes a force sensor 524, a position sensor 526, and a communication circuitry 528. The force sensor 524 may be embodied as any sensor capable of generating sensor data indicative of an amount of force applied to the sensor. For example, in one particular embodiment, the force sensor 524 is embodied as a pressure sensor such as a strain gauge. However, in other embodiments, the force sensor 524 may be embodied as any other type of force sensor configured to generate data indicative of the amount of force applied to the force sensor 524.

The position sensor 526 may be embodied as any sensor capable of generating sensor data indicative of the position of the sensor 526. For example, in one particular embodiment, the position sensor 526 may be embodied as a microelectromechanical system (MEMS) sensor, such as an accelerometer, configured to generate sensor data indicative of the orientation of the position sensor 526 with respect to the Earth's gravitational field. However, in other embodiments, the position sensor 526 may be embodied as any other type of position sensor, such as optical and/or magnetic position sensors, configured to generate data indicative of the location and/or the orientation of the sensor.

The communication circuitry 528 may be substantially similar to the communication circuitry 38 of the knee sleeve 14. For example, similar to the communication circuitry 38 illustrated in FIG. 5, the communication circuitry 528 may include a transmitter (not shown). The transmitter is configured to receive the sensor data signals from the force sensor 524 and transmit the sensor data signals to a receiver such as the healthcare provider computer 524 via the communication link 522. The transmitter may be embodied as any transmitter circuitry capable of transmitting the data signals received from the force sensor 524.

In some embodiments, the force sensor circuit 520 is embodied as a stand-alone device separate from the knee sleeve 516. For example, as discussed below in more detail in regard to FIGS. 10-12, the force sensor circuit 520 may be incorporated into a glove wearable by the orthopaedic surgeon. Alternatively, the force sensor circuit 520 may be embodied as a device sized to be held by the orthopaedic surgeon. In other embodiments, the force sensor circuit 520 is coupled to the knee sleeve 14. In such embodiments, the force sensor circuit 520 may be coupled toward a distal end of the inferior half of the knee sleeve 14. As discussed in more detail below, the force sensor circuit 520 is configured to generate force data indicative of the amount of force applied to the leg of the patient by the surgeon during manipulation of the patient's leg.

The healthcare provider computer 502 includes a processor 530, memory device 532, and, in some embodiments, a display 534. The processor 530 may be embodied as any type of processor including, for example, discrete processing circuitry (e.g., a collection of logic devices), general purpose integrated circuit(s), and/or application specific integrated circuit(s) (i.e., ASICs). The memory device 532 may be embodied as any type of memory device and may include one or more memory types, such as, random access memory (i.e., RAM) and/or read-only memory (i.e., ROM). The display 534 may be embodied as any type of display or display device capable of displaying data and images to a user (e.g., an orthopaedic) of the healthcare provider computer 502. In some embodiments, the display 534 forms an integral portion of the healthcare provider computer 502. However, in other embodiments, the display 534 may be separate from the healthcare provider computer 502, but communicatively coupled therewith.

The healthcare provider computer 502 also includes communication circuitry 536 to facilitate communication with the knee sleeve 14 (via the communication circuitry 38), the manufacturer computer 506 via the network 510, and the force sensor circuit 520. As such, the communication circuitry 536 may include transmitter and/or receiver circuitry. Additionally, the communication circuitry 536 may be configured to communicate with the knee sleeve 14, the manufacturer computer 506, the force sensor circuit 530, and/or other devices using wired or wireless communication protocols depending upon, for example, the type of communication link 516, 522 and/or the type of network 510. For example, in embodiments wherein the network 510 is a wireless network, the communication circuitry 536, or portion thereof, may be embodied as a wireless communication circuitry.

Additionally, in some embodiments, the healthcare provider computer 502 may also include a portable media interface 538. The portable media interface 538 is configured to receive a portable media device 540. In the illustrative embodiment, the portable media interface 538 is embodied as a Universal Serial Bus (USB) port. However, in other embodiments, the portable media interface 538 may be embodied as any type of serial port, parallel port, flash drive port, or other data port capable of communicating with and storing data on the portable media device 540. The portable media device 540 may be embodied as any portable memory device configured for the purpose of transporting data from one computer system to another computer system. In some embodiments, the portable media memory device 540 is embodied as a removable solid-state memory device such as a removable flash memory device. For example, the portable media device 540 may be embodied as a MemoryStick™ flash memory device, a SmartMedia™ flash memory device, or a CompactFlash™ flash memory device. Alternatively, in other embodiments, the portable media device 540 may be embodied as a memory device having a microdrive for data storage. Regardless, the portable media memory device 540 is capable of storing data such as sensor data for later retrieval.

In addition, the healthcare provider computer 502 may include other devices and circuitry typically found in a computer for performing the functions described herein such as, for example, a hard drive, input/output circuitry, and the like. As such, the healthcare provider computer 502 may be embodied as any type of computer or computing device capable of receiving data from knee sleeve 14 and the force sensor circuit 520. For example, the healthcare provider computer 502 may be embodied as a typical desktop or laptop computer equipped with a display screen, keyboard, and other devices and circuitry typically found in a desktop and/or laptop computer. Alternatively, the healthcare provider computer 502 may be embodied as an application specific computer or computer device configured to perform the functions described herein. Further, in some embodiments, the healthcare provider computer 502 may form a portion of a hospital network or otherwise be communicatively coupled to such a network.

The system 500 also includes an imaging system 542 located at the healthcare facility 504. The imaging system 542 may be embodied as any type of imaging system 542 capable of generating medical images of the patient's bony anatomy. For example, the imaging system may be embodied as a computed tomography (CT) imaging device, a magnetic resonance imagining (MRI) device, or other imaging system. In some embodiments, the imagining system 542 is communicatively coupled to the vendor computer 506 via the network 510 and a number of communication links 544. In such embodiments, the communication links 544 may be embodied as any type of communication links capable of providing communication between the imaging system 542 and the manufacturer computer 506. For example, the communication links 544 may be embodied as any number of cables, wires, fiber optic cables, wireless signals, and/or the like. In some embodiments, the imagining system 542 may be communicatively coupled to a network of the healthcare facility, which in turn may be communicatively coupled to the network 510. Additionally, in some embodiments, the imaging system 542 may include a database (not shown) or otherwise be communicatively coupled to the database and configured to store the medical images in the database. In such embodiments, database may include a Patient Archiving Communications System (PACS) that stores medical images for patients of the healthcare facility 504.

The manufacturer computer 506 includes a processor 550, memory device 552, and, in some embodiments, a display 554. The processor 550 may be embodied as any type of processor including, for example, discrete processing circuitry (e.g., a collection of logic devices), general purpose integrated circuit(s), and/or application specific integrated circuit(s) (i.e., ASICs). The memory device 552 may be embodied as any type of memory device and may include one or more memory types, such as, random access memory (i.e., RAM) and/or read-only memory (i.e., ROM). The display 554 may be embodied as any type of display or display device capable of displaying data and images to a user (e.g., an orthopaedic) of the manufacturer computer 506. In some embodiments, the display 554 forms an integral portion of the manufacturer computer 506. However, in other embodiments, the display 554 may be separate from the manufacturer computer 506, but communicatively coupled therewith.

The manufacturer computer 506 also includes communication circuitry 556 to facilitate communication with healthcare provider computer 502 via the network 510. As such, the communication circuitry 556 may include transmitter and/or receiver circuitry. Additionally, the communication circuitry 556 may be configured to communicate with the healthcare provider computer 502 using wired or wireless communication protocols depending upon, for example, the type of network 510. For example, in embodiments wherein the network 510 is a wireless network, the communication circuitry 556, or portion thereof, may be embodied as a wireless communication circuitry.

Additionally, in some embodiments, the manufacturer computer 506 may also include a portable media interface 558. The portable media interface 558 is configured to receive the portable media device 540. In the illustrative embodiment, the portable media interface 558 is embodied as a Universal Serial Bus (USB) port. However, in other embodiments, the portable media interface 558 may be embodied as any type of serial port, parallel port, flash drive port, or other data port capable of communicating with and storing data on the portable media device 540. As discussed above, the portable media device 540 may be embodied as any portable memory device configured for the purpose of transporting data from one computer system to another computer system.

In addition, the manufacturer computer 506 may include other devices and circuitry typically found in a computer for performing the functions described herein such as, for example, a hard drive, input/output circuitry, and the like. As such, the manufacturer computer 506 may be embodied as any type of computer or computing device capable of receiving data from healthcare provider computer 502 via the network 510 and/or the portable media device 540. For example, the manufacturer computer 506 may be embodied as a typical desktop or laptop computer equipped with a display screen, keyboard, and other devices and circuitry typically found in a desktop and/or laptop computer. Alternatively, the manufacturer computer 506 may be embodied as an application specific computer or computer device configured to perform the functions described herein.

In use, the orthopaedic surgeon may operate the healthcare provider computer 502, the knee sleeve 14, and the force sensor circuit 520 to perform pre-operative planning on the patient's joint. That is, via use of the knee sleeve 14 and the force sensor circuit 520, the orthopedic surgeon is able to investigate the soft tissue structure of the patient's joint preoperatively. For example, the orthopaedic surgeon may utilize the knee sleeve 14, the force sensor circuit 520, and the computer 502 to determine the angulation of the patient's joint (e.g., the angle defined between the patient's femur and tibia). The joint angulation investigation may include determining the ligament laxity of the relevant joint. Such information, along with medical images of the patient's joint generated via the imaging system 542, may subsequently be provided to the manufacturer computer 506 to facilitate the design of a patient-specific orthopaedic surgical instrument. The joint angulation data, the medical images, and any additional constraint data or surgeon preferences may be transmitted to the manufacturer computer 508 via the network 510 or the portable media device 540. The manufacturer computer 508 uses the medical images, angulation data, and any additional surgeon constraint data to generate a design or model of the patient-specific orthopaedic surgical instrument. The design may be embodied as a set of instructions, such as fabrication instructions, a model, or other data that defines the embodiment of the patient-specific orthopaedic surgical instrument may be fabricated. For example, in embodiments wherein the design is embodied as a model of the instrument, the model may be a three-dimensional software model or a prototype model, which is sent to or otherwise viewable by the surgeon to determine the accuracy of the model or otherwise validate the design.

Figure 9:
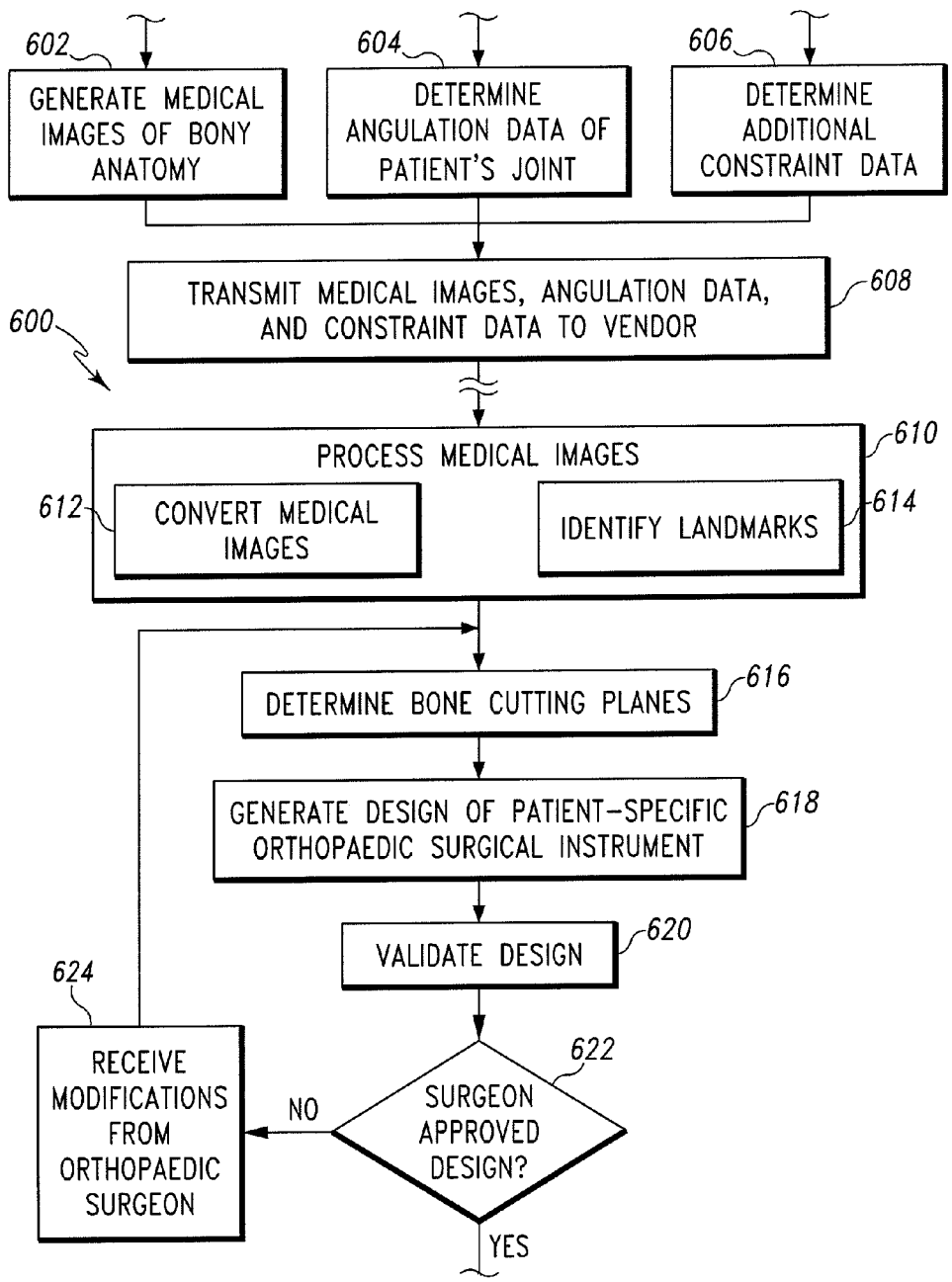
FIG. 9 is a simplified block diagram of an algorithm for designing a patient-specific orthopaedic surgical instrument.

Referring now to FIG. 9, a method 600 for designing a patient-specific orthopaedic surgical instrument includes a number of process steps 602, 604, 606 in which the orthopaedic surgeon performs an amount of pre-operative planning. The process steps 602, 604, 606 may be completed in any order or contemporaneously with each other. In process step 602, a number of medical images of the relevant bony anatomy or joint of the patient are generated. To do so, the orthopaedic surgeon or other healthcare provider may operate the imaging system 542 to generate the medical images. The medical images may be embodied as any number and type of medical images capable of being used to generate a three-dimensional model of the patient's joint. For example, the medical images may be computed tomography (CT) images, magnetic resonance imaging (MRI) images, or other type of medical images. The medical images may be stored in a suitable database, in the healthcare provider computer 502, or other suitable storage facility.

Figure 10:
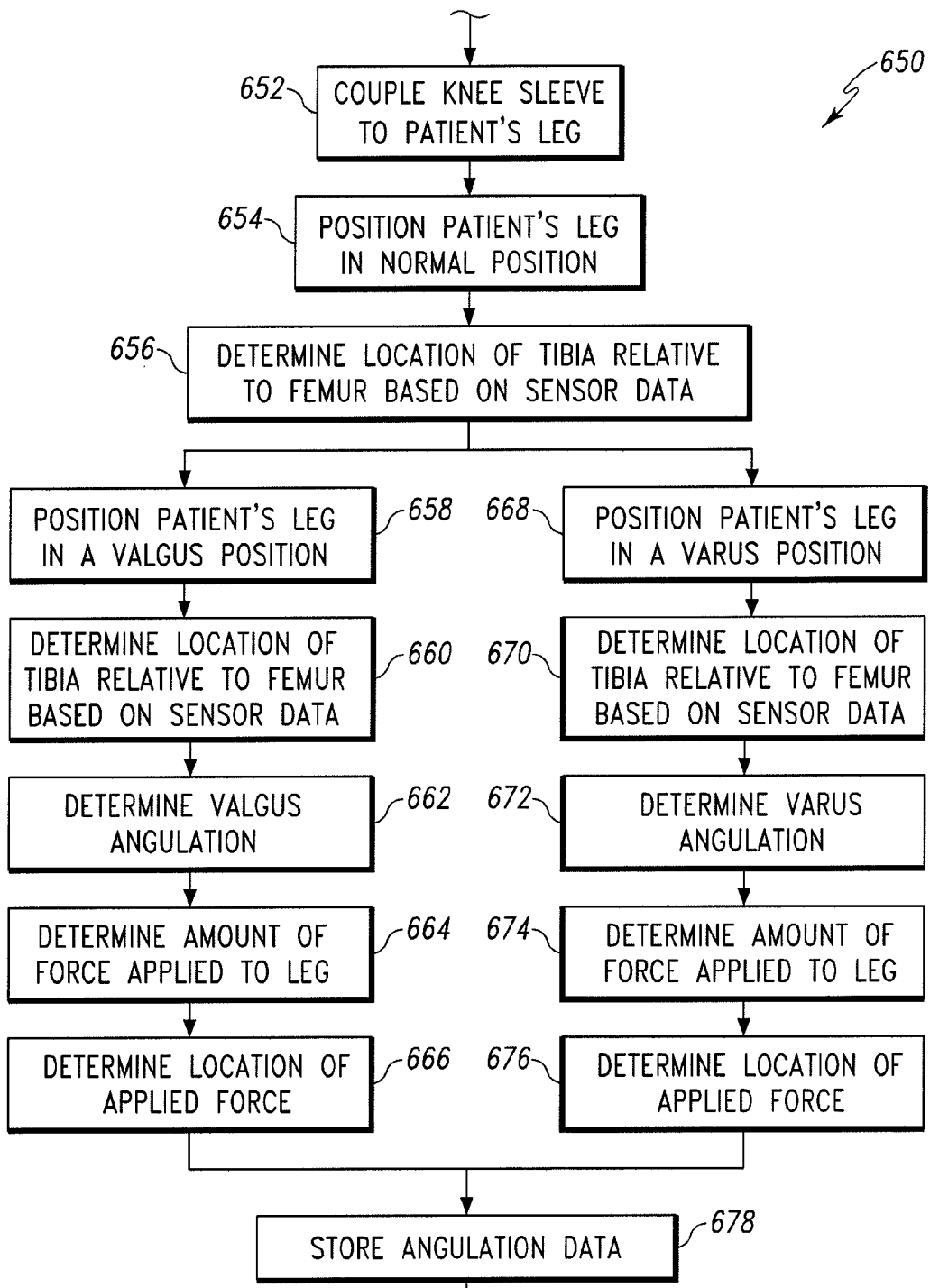
FIG. 10 is a simplified block diagram of an algorithm for determining a angulation of the patient's joint.

In process step 604, the orthopaedic surgeon determines the angulation of the patient's joint. For example, the orthopaedic surgeon may determine the ligament laxity of the relevant patient's joint. Such information is subsequently used in the designing of the patient-specific orthopaedic surgical instrument. To determine the angulation data, the orthopaedic surgeon may utilize an algorithm 650 for determining angulation data related to the patient's joint as illustrated in FIG. 10.

The algorithm 650 begins with a process step 652 in which the knee sleeve 14 is coupled to the patient's leg. After the knee sleeve 14 has been coupled to the patient, the orthopaedic surgeon positions the patient's leg in the normal anatomical position in process step 654. In process step 656, the healthcare provider computer 502 is configured to calculate the position of the relevant bones or bony anatomy (e.g., the patient's tibia and femur) of the patient based on the sensor data received from the knee sleeve 14. For example, the healthcare provider computer 502 may be configured to determine the position of the relevant femur and the tibia of the patient relative to each other based on the sensor data generated by the position sensors 92 of the sensor circuits 30, 32, 34, 36. In embodiments wherein the position sensors 92 are embodied as accelerometers generating data indicative of the position of the position sensor 92 relative to the Earth's gravitational field, the healthcare provider computer 502 may determine the relative position of the patient's femur and tibia by comparing the sensor data generated by those sensor circuits 30, 34 positioned on the superior half of the knee sleeve 14 and those sensor circuits 32, 36 positioned on the inferior half of the knee sleeve 14. By determining the location of the patient's boney anatomy in the natural anatomical position, the healthcare provider computer 502 establishes a reference from which deviation, such as valgus and/or varus angulation, can be determined as discussed below.

After the patient's leg is positioned in the normal anatomical position, the surgeon may manipulate the patient's leg to investigate the soft tissue structure of the relevant joint. That is, the orthopaedic surgeon may position the patient's leg in a valgus position (see steps 658-666) and a varus position (see steps 668-676) to determine the ligament laxity of the patient's knee. The orthopaedic surgeon may position the patient's leg in the valgus and varus positions in any order (e.g., valgus position first or varus position first).

Figure 11:
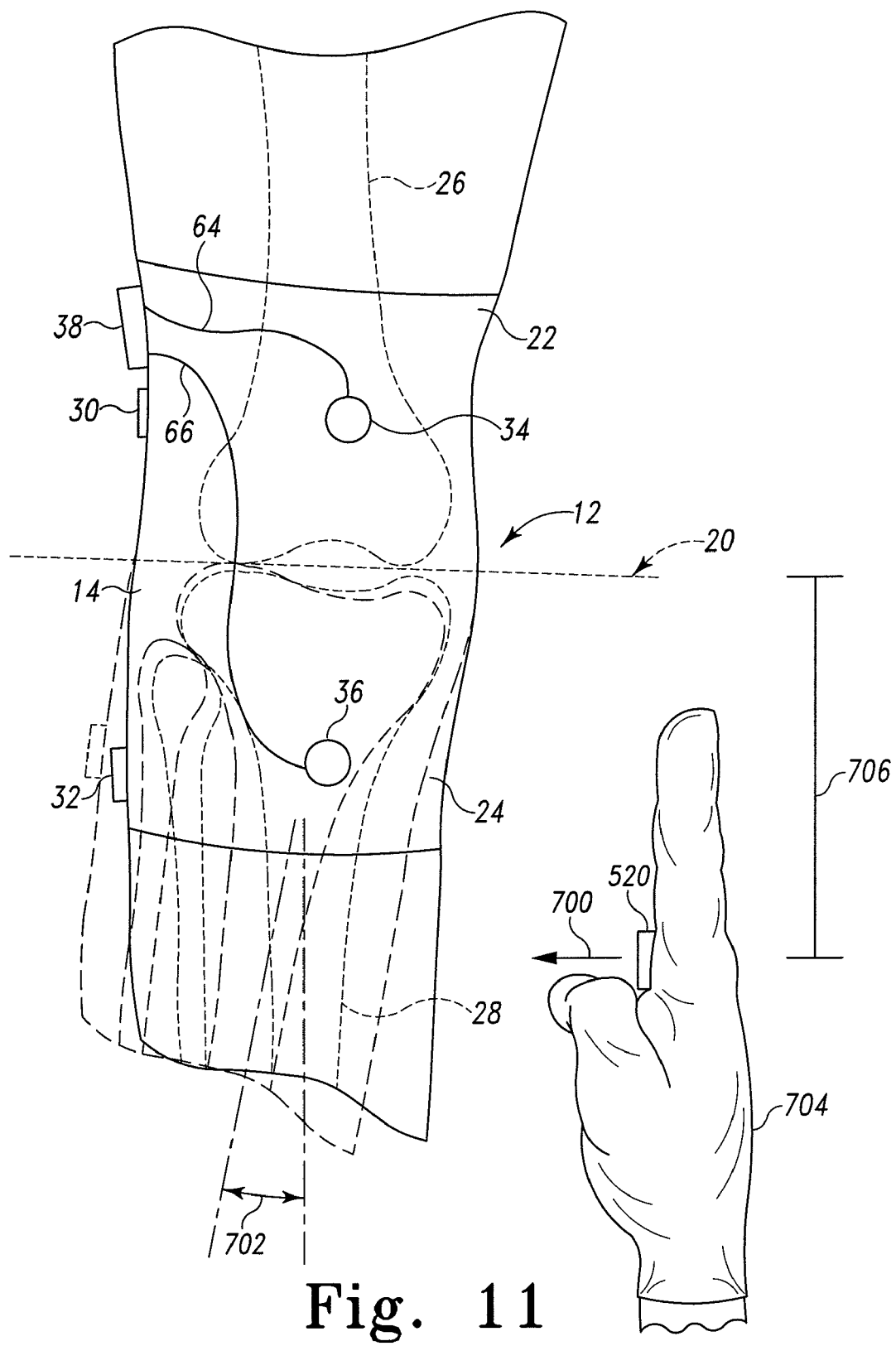
FIG. 11 is an anterior elevation view of a joint of the patient shown in one position of manipulation.

For example, as illustrated in step 658, the orthopaedic surgeon positions the patient's leg in a valgus position by applying an amount of force at a location on the patient's lower leg. As illustrated in FIG. 11, when the orthopaedic surgeon applies the amount of force 700 to the patient's leg, the leg is moved in the lateral direction such that the femur 28 of the patient defines an angle 702 between the valgus position (illustrated in phantom) and the normal anatomical position (illustrated in solid) of the femur 28. In process step 660, the healthcare provider computer 502 is configured to calculate the position of the relevant bones or bony anatomy (e.g., the patient's tibia and femur) of the patient based on the sensor data received from the knee sleeve 14. For example, as discussed above, the healthcare provider computer 502 may be configured to determine the position of the relevant femur and the tibia of the patient relative to each other based on the sensor data generated by the position sensors 92 of the sensor circuits 30, 32, 34, 36.

After the positions of the femur and tibia have been determined in process step 650, the healthcare provider computer 502 is configured to determine the valgus angulation of the patient' joint in process step 662. To do so, the healthcare provider computer 502 may be configured to calculate the angle 702, or other data indicative of the valgus angulation, based on the position of the femur and tibia in the valgus position relative to position of the femur and tibia in the normal anatomical position. For example, the healthcare provider computer 502 may be configured to compare the position data of the tibia and the femur in the normal anatomical position and the valgus position.

In process step 664, the amount of force 700 applied to the patient's leg by the orthopaedic surgeon required to position the patient's leg in the valgus position is determined. To do so, the force sensor circuit 520 is used by the orthopaedic surgeon. The force sensor circuit 520 is position between the orthopaedic surgeon's hand and the patient's leg such that the amount of force applied by the surgeon may be determined. As discussed above, in some embodiments, the force sensor circuit 520 may be incorporated into a glove 704 worn by the orthopaedic surgeon. In such embodiments, the force sensor circuit 520 (i.e., the force sensor 524) is positioned on the glove such that the circuitry 520 is positioned between the orthopaedic surgeon's hand and the patient's leg. In other embodiments, the force sensor circuit 520 may be coupled to the knee sleeve 14. In such embodiments, the orthopedic surgeon applies the amount of force 700 to the patient's leg on the location of the force sensor circuit 520. As discussed above in regard to FIG. 8, the force sensor circuit 520 is configured to transmit the force data generated in response to the application of the force 700 by the orthopaedic surgeon to the healthcare provider computer 502.

In addition to the amount of force 700 applied by the surgeon, the location of the application of the force 700 is determined in process step 666. For example, as illustrated in FIG. 11, the distance 706 at which the force 700 is applied to the patient's leg with respect to a predetermined reference point may be determined. To do so, in one embodiment, the healthcare provider computer 502 is configured to determine a center point of the knee sleeve 14 based on the sensor data received from the sensor circuits 30, 32, 34, 36. For example, the healthcare provider computer 502 may determine the central location point in the coordinate system defined by the sensor circuits 30, 32, 34, 36. The healthcare provider computer 502 may also determine the position of the force sensor circuit 520 based on the sensor data received from the position sensor 526 of the circuit 520. The healthcare provider computer 520 may calculate the distance 706 based on the position of the force sensor circuit 520 relative to the predetermined location (e.g., the central location point in the coordinate system defined by the sensor circuits 30, 32, 34, 36). After the valgus angulation has been determined in process step 662, the amount of force 700 applied to the patient's leg has been determined in process step 664, and the location of the applied force 700 has been determined in process step 666, the healthcare provider computer 502 stores the angulation data (i.e., the angle 702, the amount of force 700, and the distance 706) in process step 678. The healthcare provider computer 502 may store the angulation data in the memory 532, in a database, or other suitable location.

Figure 12:
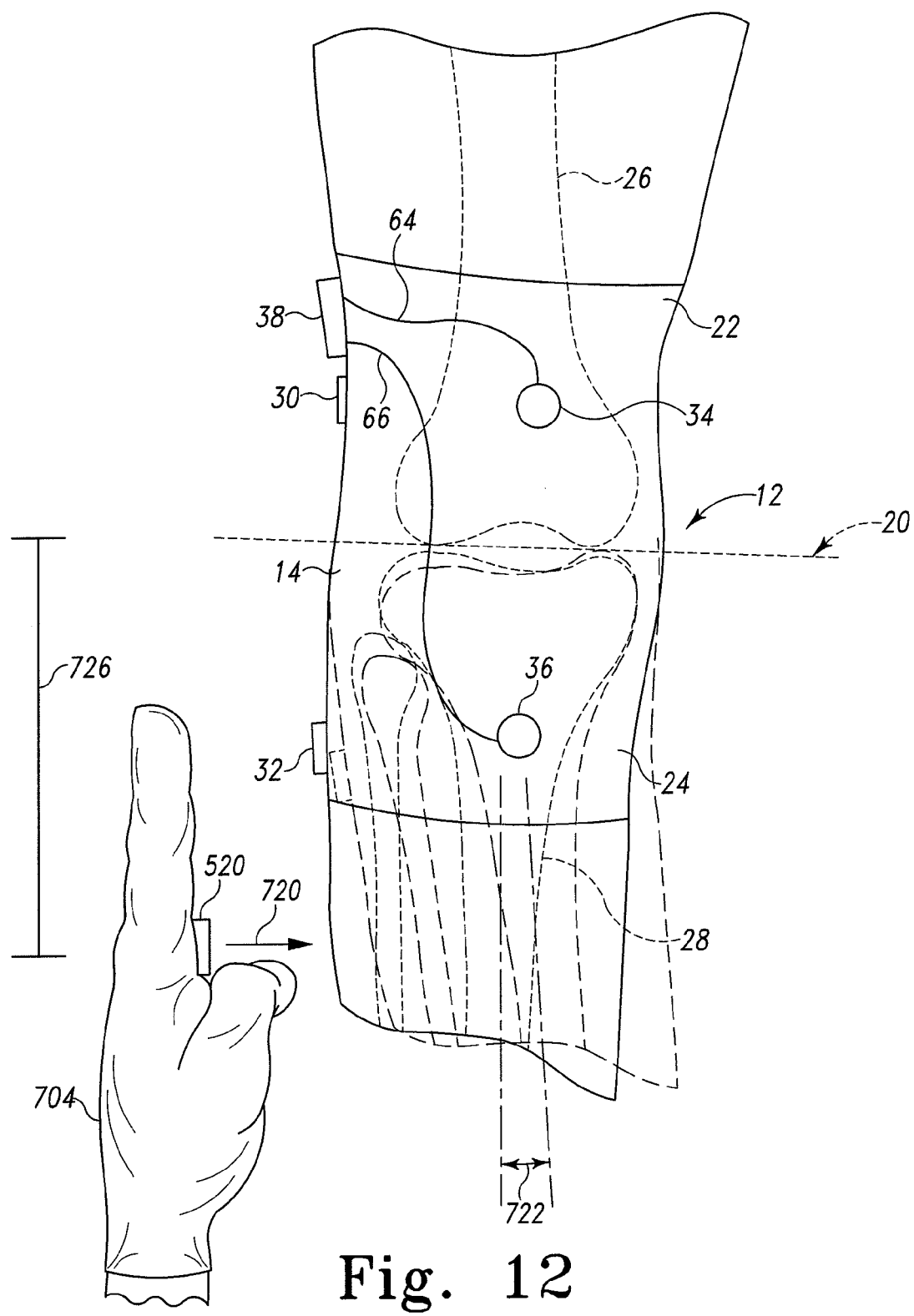
FIG. 12 is an anterior elevation view of the joint of the patient of FIG. 11 shown in another position of manipulation.

As discussed above, the orthopaedic surgeon also positions the patient's leg in a varus position by applying an amount of force at a location on the patient's lower leg in process step 668. As illustrated in FIG. 12, when the orthopaedic surgeon applies the amount of force 720 to the patient's leg, the leg is moved in the medial direction such that the femur 28 of the patient defines an angle 722 between the varus position (illustrated in phantom) and the normal anatomical position (illustrated in solid) of the femur 28. In process step 670, the healthcare provider computer 502 is configured to calculate the position of the relevant bones or bony anatomy (e.g., the patient's tibia and femur) of the patient based on the sensor data received from the knee sleeve 14. As discussed above, the healthcare provider computer 502 may be configured to determine the position of the relevant femur and the tibia of the patient relative to each other based on the sensor data generated by the position sensors 92 of the sensor circuits 30, 32, 34, 36.

After the positions of the femur and tibia have been determined in process step 670, the healthcare provider computer 502 is configured to determine the varus angulation of the patient' joint in process step 672. To do so, the healthcare provider computer 502 may be configured to calculate the angle 722, or other data indicative of the varus angulation, based on the position of the femur and tibia in the varus position relative to position of the femur and tibia in the normal anatomical position. For example, the healthcare provider computer 502 may be configured to compare the position data of the tibia and the femur in the normal anatomical position and the varus position.

In process step 674, the amount of force 720 applied to the patient's leg by the orthopaedic surgeon required to position the patient's leg in the varus position is determined. As discussed above, the force sensor circuit 520 is position between the orthopaedic surgeon's hand and the patient's leg such that the amount of force applied by the surgeon may be determined. As discussed above in regard to FIG. 11, the force sensor circuit 520 is configured to transmit the force data generated in response to the application of the force 720 by the orthopaedic surgeon to the healthcare provider computer 502.

In addition to the amount of force 720 applied by the surgeon, the location of the application of the force 720 is determined in process step 676. For example, as illustrated in FIG. 12, the distance 726 at which the force 720 is applied to the patient's leg with respect to a predetermined reference point may be determined. As discussed above, the healthcare provider computer 502 may be configured to determine a center point of the knee sleeve 14 based on the sensor data received from the sensor circuits 30, 32, 34, 36. The healthcare provider computer 502 is also configured to determine the position of the force sensor circuit 520 based on the sensor data received from the position sensor 526 of the circuit 520. The healthcare provider computer 520 may calculate the distance 726 based on the position of the force sensor circuit 520 relative to the predetermined location (e.g., the central location point in the coordinate system defined by the sensor circuits 30, 32, 34, 36). After the varus angulation has been determined in process step 672, the amount of force 720 applied to the patient's leg has been determined in process step 674, and the location of the applied force 720 has been determined in process step 676, the healthcare provider computer 502 stores the angulation data (i.e., the angle 732, the amount of force 730, and the distance 736) in process step 678. As discussed above, the healthcare provider computer 502 may store the angulation data in the memory 532, in a database, or other suitable location.

It should be appreciated that the algorithm 650 described above is typically performed on a stationary patient. That is, the patient will typically be in a seated or prone position to allow the orthopaedic surgeon to position the patient's leg as desired (i.e., position the leg in the valgus and varus position). However, in some embodiments, the orthopaedic surgeon may also desire to obtain angulation data of the patient's joint in a standing position. That is, the surgeon may investigate the alignment of the patient's femur and tibia in the standing position. When the patient is in the standing position, the weight exerted on the patient's joint may cause deformity of the alignment of the joint.

As discussed above, the knee sleeve 14 may be used to determine the angulation data of the patient's joint in the standing position. That is, as discussed above, the healthcare provider computer 502 is configured to calculate the position of the relevant bones or bony anatomy (e.g., the patient's tibia and femur) of the patient based on the sensor data received from the knee sleeve 14. The angulation data of the patient's joint in the standing position may be used in addition to, or in place of, the valgus/varus angulation data determined in algorithm 650. Regardless, the angulation data of the patient's joint determined with the patient in the standing position may be used to facilitate or modify the design of the patient-specific orthopaedic surgical instrument in some embodiments.

Additionally, in some embodiments, the orthopaedic surgeon may also desire to obtain angulation data of the patient's joint dynamically. That is, the angulation data of the patient's joint may be obtained while the patient is in motion. To do so, the knee sleeve 14 may be coupled to the patient's relevant knee and the patient may perform an exercise such as walking on a treadmill. The healthcare provider computer 502 may be configured to collect and store the sensor data generated while the patient is exercising. The computer 502 may store such data in, for example, the memory device 532. As discussed above, the computer 502 is configured to calculate the position of the relevant bones or bony anatomy (e.g., the patient's tibia and femur) of the patient based on the sensor data received from the knee sleeve 14. As with the angulation data generated while the patient is in the standing position, the dynamic angulation data may be used in addition to, or in place of, the valgus/varus angulation data determined in algorithm 650. Regardless, the angulation data of the patient's joint determined while the patient is walking or otherwise exercising may be used to facilitate or modify the design of the patient-specific orthopaedic surgical instrument in some embodiments.

Referring back to FIG. 9, the orthopaedic surgeon may also determine any additional pre-operative constraint data in process step 606 of algorithm 600. The constraint data may be based on the orthopaedic surgeon's preferences, preferences of the patient, anatomical aspects of the patient, guidelines established by the healthcare facility, or the like. For example, constraint data may include the orthopaedic surgeon's preference for a metal-on-metal interface, amount of inclination for implantation, size range of the orthopaedic implant, and/or the like.

In process step 608, the medical images, the angulation data, and the constraint data, if any, are transmitted to the manufacturer computer 506. The medical images, the angulation data, and the constraint data may be transmitted to the manufacturer computer 506 via the network 510 and the communication links 512, 514, 544. Additionally or alternatively, the medical images, the angulation data, and/or the constraint data may be stored on the portable media device 540 or similar storage device and transferred to the manufacturer computer 506.

After the vendor has received the medical images and the constraint data, the vendor processes the images in step 610. The orthopaedic surgical instrument vendor or manufacturer processes the medical images to facilitate the determination of the bone cutting planes, implant sizing, and design of the customized patient-specific orthopaedic surgical instrument as discussed in more detail below. For example, in process step 612 the vendor may convert or otherwise generate three-dimensional images from the medical images. For example, in embodiments wherein the medical images are embodied as a number of two-dimensional images, the vendor may use a suitable computer algorithm to generate one or more three-dimensional images form the number of two-dimensional images. Additionally, in some embodiments, the medical images may be generated based on an established standard such as the Digital Imaging and Communications in Medicine (DICOM) standard. In such embodiments, an edge-detection algorithm may be used to convert or reconstruct images to a format acceptable in a computer aided design application or other image processing application.

In process step 614, the vendor may process the medical images, and/or the converted/reconstructed images from process step 20, to determine a number of aspects related to the bony anatomy of the patient such as the anatomical axis of the patient's bones, the mechanical axis of the patient's bone, other axes and various landmarks, and/or other aspects of the patient's bony anatomy. To do so, the manufacturer may use any suitable algorithm to process the images.

In process step 616, the cutting planes of the patient's bone are determined. The planned cutting planes are determined based on the type, size, and position of the orthopaedic prosthesis to be used during the orthopaedic surgical procedure, on the process images such as specific landmarks identified in the images, and on the constraint data supplied by the orthopaedic surgeon in process steps 606 and 608. The type and/or size of the orthopaedic prosthesis may be determined based on the patient's anatomy and the constraint data. For example, the constraint data may dictate the type, make, model, size, or other characteristic of the orthopaedic prosthesis. The selection of the orthopaedic prosthesis may also be modified based on the medical images such that an orthopaedic prosthesis that is usable with the bony anatomy of the patient and that matches the constraint data or preferences of the orthopaedic surgeon is selected.

In addition to the type and size of the orthopaedic prosthesis, the planned location and position of the orthopaedic prosthesis relative to the patient's bony anatomy is determined. To do so, a digital template of the selected orthopaedic prosthesis may be overlaid onto one or more of the processed medical images. The manufacturer or vendor may use any suitable algorithm to determine a recommended location and orientation of the orthopaedic prosthesis (i.e., the digital template) with respect to the patient's bone based on the processed medical images (e.g., landmarks of the patient's bone defined in the images) and/or the constraint data. Additionally, any one or more other aspects of the patient's bony anatomy may be used to determine the proper positioning of the digital template.

The planned cutting planes for the patient's bone(s) may then be determined based on the determined size, location, and orientation of the orthopaedic prosthesis. In addition, other aspects of the patient's bony anatomy, as determined in process step 614, may be used to determine or adjust the planned cutting planes. For example, the determined mechanical axis, landmarks, and/or other determined aspects of the relevant bones of the patient may be used to determine the planned cutting planes.

Further, in process step 616, the location and orientation of the planned cutting planes may be adjusted or otherwise determined based on the angulation data. That is, the manufacturer computer 506 may be configured to adjust the location and/or orientation of the digital template or planned cut planes of the orthopaedic prosthesis relative to the patient's bony anatomy by any amount based on the angulation data. For example, if the angulation data indicates that the patient's joint has a large degree of ligament laxity, the position of digital template, and thus the position of the orthopaedic prosthesis, relative to the patient's bony anatomy may be adjusted to compensate for the laxity of the joint. Because the manufacturer computer 506 has access to the valgus and varus angulation, amount of force applied, and location of the applied force, the amount of repositioning required to compensate for the soft tissue structure of the patient's joint may be calculated by the computer 506.

In process step 618, a design of the patient-specific orthopaedic surgical instrument is generated. As discussed above, the design may be embodied as a set of instructions, such as fabrication instructions, a model, or other data that defines the embodiment of the patient-specific orthopaedic surgical instrument may be fabricated. For example, in some embodiments, the design is embodied as a three-dimensional rendering of the customized patient-specific orthopaedic surgical instrument. In other embodiments, the design may be embodied as a mock-up or fast prototype model of the customized patient-specific orthopaedic surgical instrument. The particular type of orthopaedic surgical instrument to be modeled and fabricated may be determined based on the orthopaedic surgical procedure to be performed, the constraint data, and/or the type of orthopaedic prosthesis to be implanted in the patient. As such, the patient-specific orthopaedic surgical instrument may be embodied as any type of orthopaedic surgical instrument for use in the performance of an orthopaedic surgical procedure. For example, the orthopaedic surgical instrument may be embodied as a bone-cutting block, a drilling guide, a milling guide, and/or the any other type of orthopaedic surgical tool or instrument.

The particular shape of the customized patient-specific orthopaedic surgical instrument is determined based on the planned location of the orthopaedic surgical instrument relative to the patient's bony anatomy. The location of the customized patient-specific orthopaedic surgical instrument with respect to the patient's bony anatomy is determined based on the type and determined location of the orthopaedic prosthesis to be used during the orthopaedic surgical procedure. That is, the planned location of the customized patient-specific orthopaedic surgical instrument relative to the patient's bony anatomy may be selected based on, in part, the planned cutting planes of the patient's bone(s) as determined in step 616. For example, in embodiments wherein the customized patient-specific orthopaedic surgical instrument is embodied as a bone-cutting block, the location of the orthopaedic surgical instrument is selected such that the cutting guide of the bone-cutting block matches one or more of the planned cutting planes determined in process step 616. It should be appreciated, however, that in other embodiments additional data may be used to determine the bone cutting planes and/or the design of the patient-specific orthopaedic surgical instrument.

Figure 13:
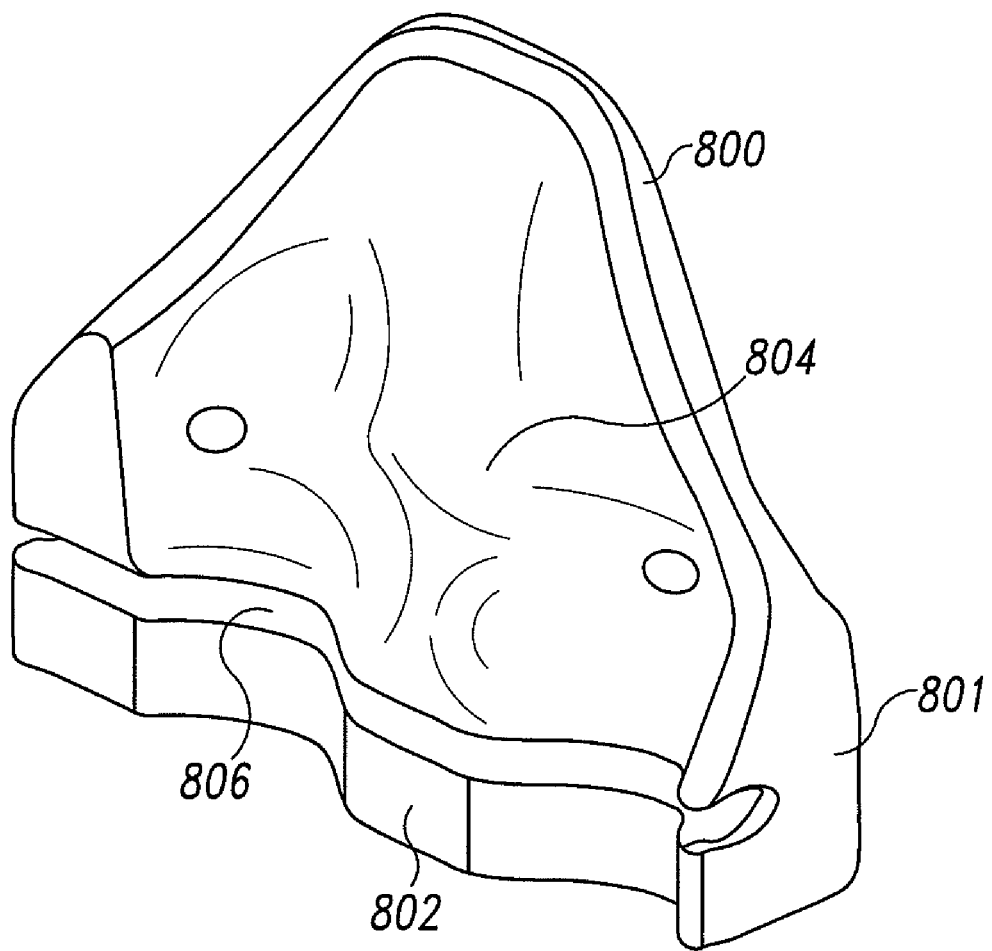
FIG. 13 is a perspective view of one embodiment of a patient customized orthopaedic surgical tool fabricated according to the algorithm of FIG. 9.

When the orthopaedic surgical instrument is coupled to the patient's boney anatomy in the unique location, any guide (e.g., cutting or drilling guide) of the patient-specific orthopaedic surgical instrument is aligned to the cutting plane(s) determined in process steps 616 as discussed above. For example, as illustrated in FIG. 13, the patient-specific orthopaedic surgical instrument may be embodied as a bone-cutting guide 800 in one embodiment. The bone-cutting guide 800 includes a body 801 having a bone-contacting surface 802. A negative contour 804 is defined in the bone-contacting surface 802. The negative contour 804 matches the contour of a portion of the patient's bony anatomy such that, when the bone-cutting guide 800 is coupled to the patient's bony anatomy, the portion of the patient's bony anatomy is received in the recess defined by the negative contour 804. The bone-cutting guide 800 also includes a cutting slots or guide 806 defined in the block. Any cut made using the cutting guide 806 corresponds to one or more of the planned cutting planes determined in process step 616, which may have been adjusted to compensate for the ligament laxity of the patient's joint as discussed above.

After the design of the patient-specific orthopaedic surgical instrument has been generated in process step 618, the design is validated in process step 620. The design may be validated by, for example, analyzing the rendered model while coupled to the three-dimensional model of the patient's anatomy to verifying the correlation of cutting guides and planes, drilling guides and planned drill points, and/or the like. Additionally, the design may be validated by transmitting or otherwise providing the design generated in step 618 to the orthopaedic surgeon for review. For example, in embodiments wherein the model is a three-dimensional rendered model, the model along with the three-dimensional images of the patient's relevant bone(s) may be transmitted to the surgeon for review. In embodiments wherein the model is a physical prototype, the model may be shipped to the orthopaedic surgeon for validation.

The orthopaedic surgeon may analyze the calculations and decisions determined by the manufacturer computer 506; the type and placement of the orthopedic prosthesis relative to the patient's bony anatomy; the type, design, and placement of the patient-specific orthopaedic surgical instrument relative to the patient's boney anatomy; and/or any other relevant data to determine the accuracy of such calculations and determinations. If the orthopaedic surgeon desires changes to the orthopaedic prosthesis, the customized patient orthopaedic surgical instrument, or placement thereof, the orthopaedic surgeon may transmit or otherwise provide such modifications to the manufacture facility 508 in process step 624. If so, the algorithm loops back to process step 616 wherein the manufacturer computer 506 re-determines the cutting planes and re-designs the patient-specific orthopaedic surgical instrument again based on the orthopaedic surgeon's modifications. However, if no modifications are required, the algorithm 600 completes. The design of the patient-specific orthopaedic surgical instrument may subsequently be used to fabricate the instrument in another process.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, device, and system described herein. It will be noted that alternative embodiments of the method, device, and system of the present disclosure may not include all of the features described yet still benefit from at least some of the advantages of such features. Those of ordinary skill in the art may readily devise their own implementations of the method, device, and system that incorporate one or more of the features of the present invention and fall within the spirit and scope of the present disclosure as defined by the appended claims.

The invention claimed is:

1. A method for designing a patient-specific orthopaedic surgical instrument to be used on a knee of a patient, the method comprising:
    coupling a knee sleeve to a leg of the patient, the knee sleeve including (i) a first sensor coupled to a superior half of the knee sleeve and generating first data indicative of the position of the first sensor and (ii) a second sensor coupled to an inferior half of the knee sleeve and generating second data indicative of the position of the second sensor;
    generating, using a force sensor separate from the knee sleeve, force data indicative of an amount of force applied to the leg of the patient;
    determining angulation data indicative of the angulation of the knee of the patient based on the first data, the second data, and the force data;
    generating a medical image of the knee of the patient; and
    determining a design of a patient-specific orthopaedic surgical instrument based on the medical image and the angulation data.

2. The method of claim 1, wherein determining the angulation data comprises:
    (i) determining valgus data indicative of an amount of valgus angulation of the leg of the patient, and
    (ii) determining varus data indicative of an amount of varus angulation of the leg of the patient.

3. The method of claim 2, wherein:
    determining valgus data comprises determining valgus data indicative of the amount of valgus angulation of the leg of the patient with respect to a first amount of force applied to the leg at a first location on the leg, and
    determining varus data comprises determining varus data indicative of the amount of varus angulation of the leg of the patient with respect to a second amount of force applied to the leg at a second location on the leg.

4. The method of claim 1, wherein determining the angulation data comprises determining data indicative of the ligament laxity of the knee.

5. The method of claim 1, wherein determining the angulation data comprises determining the position of the femur of the leg of the patient based on the first data and determining the position of the tibia of the leg of the patient based on the second data.

6. The method of claim 1, wherein determining the angulation data comprises:
applying an amount of force to the leg of the patient at a location on the leg to position the leg of the patient in a valgus position;
generating angle data indicative of the valgus angulation of the leg when in the valgus position; and
generating location data indicative of the location on the leg at which the force is applied relative to a predetermined location.

7. The method of claim 1, wherein determining the angulation data comprises:
applying an amount of force to the leg of the patient at a location on the leg to position the leg of the patient in a varus position;
generating angle data indicative of the varus angulation of the leg when in the varus position; and
generating location data indicative of the location on the leg at which the force is applied relative to a predetermined location.

8. The method of claim 1, wherein determining angulation data comprises determining the position of the femur of the leg of the patient based on the first data and determining the position of the tibia of the leg of the patient based on the second data while the patient is in a standing position.

9. The method of claim 1, wherein determining angulation data comprises determining the position of the femur of the leg of the patient based on the first data and determining the position of the tibia of the leg of the patient based on the second data while the patient is in motion.

10. The method of claim 1, further comprising determining constraint data indicative of preferences of an orthopaedic surgeon, wherein determining a design of a patient-specific orthopaedic surgical instrument comprises determining a design of a patient-specific orthopaedic surgical instrument based on the medical image, the angulation, and the constraint data.

11. The method of claim 1, wherein determining a design of a patient-specific orthopaedic surgical instrument comprises adjusting the location of a cutting guide of a bone cutting block based on the angulation data.

12. A system for designing a patient-specific orthopaedic surgical instrument to be used on a knee of a patient, the system comprising:
a knee sleeve configured to be coupled to a leg of the patient;
a first sensor coupled to the knee sleeve and configured to generate first data indicative of the position of the first sensor;
a second sensor coupled to the knee sleeve and configured to generate second data indicative of the position of the second sensor;
a force sensor incorporated into a glove and configured to generate force data indicative of an amount of force applied to the leg of the patient; and
a first computer configured to (i) determine angle data indicative of the degree of angulation between the femur and the tibia of the patient's leg based on the first data and the second data, (ii) determine location data indicative of the location of the force sensor relative to a predetermined location, and (iii) store the angle data, force data, and location data.

13. The system of claim 12, wherein the first computer is configured to (i) determine third data indicative of the position of the femur of the leg of the patient based on the first data and (ii) determine fourth data indicative of the position of the tibia of the leg of the patient.

14. The system of claim 12, further comprising a second computer remote from the first computer, the second computer configured to generate a three-dimensional model of the patient-specific surgical instrument based on the angle data, force data, and location data.

15. A method for designing a patient-specific orthopaedic surgical instrument, the method comprising:
coupling a knee sleeve to a leg of the patient, the knee sleeve including (i) a first sensor coupled to a superior half of the knee sleeve and generating first data indicative of the position of the first sensor and (ii) a second sensor coupled to an inferior half of the knee sleeve and generating second data indicative of the position of the second sensor
generating force data indicative of an amount of force applied to the leg of the patient using a force sensor incorporated into a glove;
generating laxity data indicative of the ligament laxity of the knee of the patient based on the first data, the second data, and the force data; and
generating a design of a patient-specific orthopaedic instrument based on the laxity data.

16. The method of claim 15, further comprising generating a medical image of the patient's knee, wherein generating a design of the patient-specific orthopaedic instrument comprises generating a design of the patient-specific orthopaedic instrument based on the laxity data and the medical image.

17. The method of claim 15, wherein generating laxity data comprises:
applying a first amount of force to the leg at a first location on the leg to position the leg of the patient in a valgus position,
generating first angle data indicative of the valgus angulation of the leg when in the valgus position,
generating first force data indicative of the first amount of force using the force sensor incorporated into the glove,
generating first location data indicative of the first location relative to a predetermined location,
applying a second amount of force to the leg at a second location on the leg to position the leg of the patient in a varus position,
generating second angle data indicative of the varus angulation of the leg when in the varus position,
generating second force data indicative of the second amount of force using the force sensor incorporated into the glove, and
generating second location data indicative of the second location relative to the predetermined location,
wherein generating a design of the patient-specific orthopaedic instrument comprises generating a design of the patient-specific orthopaedic instrument based on the first angle data, the first force data, the first location data, the second angle data, the second force data, and the second location data.

* * * * *